United States Patent
Stephanou

(10) Patent No.: US 9,880,133 B1
(45) Date of Patent: Jan. 30, 2018

(54) NON-DESTRUCTIVE ULTRASONIC YIELD STRENGTH MEASUREMENT TOOL

(71) Applicant: Atlas Sensors, LLC, Sunnyvale, CA (US)

(72) Inventor: Philip J. Stephanou, Mountain View, CA (US)

(73) Assignee: Atlas Sensors, LLC, Sunnyvale, CA (US)

( * ) Notice: Subject to any disclaimer, the term of this patent is extended or adjusted under 35 U.S.C. 154(b) by 298 days.

(21) Appl. No.: 14/637,101

(22) Filed: Mar. 3, 2015

Related U.S. Application Data

(60) Provisional application No. 61/948,083, filed on Mar. 5, 2014.

(51) Int. Cl.
| | |
|---|---|
| *G01F 17/00* | (2006.01) |
| *G01N 29/04* | (2006.01) |
| *G01N 29/44* | (2006.01) |
| *G01N 3/00* | (2006.01) |

(52) U.S. Cl.
CPC .............. *G01N 29/04* (2013.01); *G01N 3/00* (2013.01); *G01N 29/44* (2013.01)

(58) Field of Classification Search
None
See application file for complete search history.

(56) References Cited

U.S. PATENT DOCUMENTS

| | | | | | |
|---|---|---|---|---|---|
| 3,402,598 | A | * | 9/1968 | Colgate | G01N 29/221 73/629 |
| 3,872,330 | A | * | 3/1975 | Miller | B06B 1/0215 310/316.03 |
| 5,143,072 | A | * | 9/1992 | Kantorovich | G01H 5/00 600/437 |

* cited by examiner

*Primary Examiner* — Cory Eskridge
(74) *Attorney, Agent, or Firm* — Van Pelt, Yi & James LLP

(57) ABSTRACT

A system for determining a material property is disclosed. In some embodiments, a method for determining a material property comprises receiving a set of material responses corresponding to a set of ultrasonic excitations. The set of material responses are determined using measurements to determine a peak response for each of the set of ultrasonic excitations. In some embodiments, a device for making non-destructive in-situ measurements of the elastic yield strength of a sample (e.g., a steel plate or pipeline wall) is disclosed. The device determines the yield strength of a specimen based on transducing ultrasonic waves within the medium and correlating quantifiable characteristics of the resulting frequency response to the intrinsic elastic nonlinearity of the material. In various embodiments, the device includes one or more electrodes, an acoustic termination, a horn, a flange, a collar, power electronics, signal processors, a memory, a user interface, or any other appropriate device component.

21 Claims, 26 Drawing Sheets

NON-DESTRUCTIVE ULTRASONIC YIELD STRENGTH MEASUREMENT TOOL

This application claims priority to U.S. Provisional Patent Application No. 61/948,083 entitled NON-DESTRUCTIVE ULTRASONIC YIELD STRENGTH MEASURMENT TOOL filed Mar. 5, 2014 which is incorporated herein by reference for all purposes.

BACKGROUND

Measurement techniques utilizing ultrasonic waves have advantages in being able to be employed in-situ and have substantially no permanent effect on a sample. However, current ultrasonic non-destructive evaluation (NDE) and non-destructive test (NDT) techniques typically give indirect indications of variations of mechanical properties and morphological conditions within a sample. Moreover, empirical correlations and calibration factors may also need to be established for each sample material. For example, ultrasonic NDE/NDT techniques are used to measure such quantities as time of flight and attenuation, from which information about phase velocity (itself dependent on stiffness and density) and discontinuities (such as cracks and boundaries) may be inferred. However, the empirical correlations, calibrations factors, and other assumptions are potentially significant sources of error in the inferences made.

BRIEF DESCRIPTION OF THE DRAWINGS

Various embodiments of the invention are disclosed in the following detailed description and the accompanying drawings.

DETAILED DESCRIPTION

Figure 1:
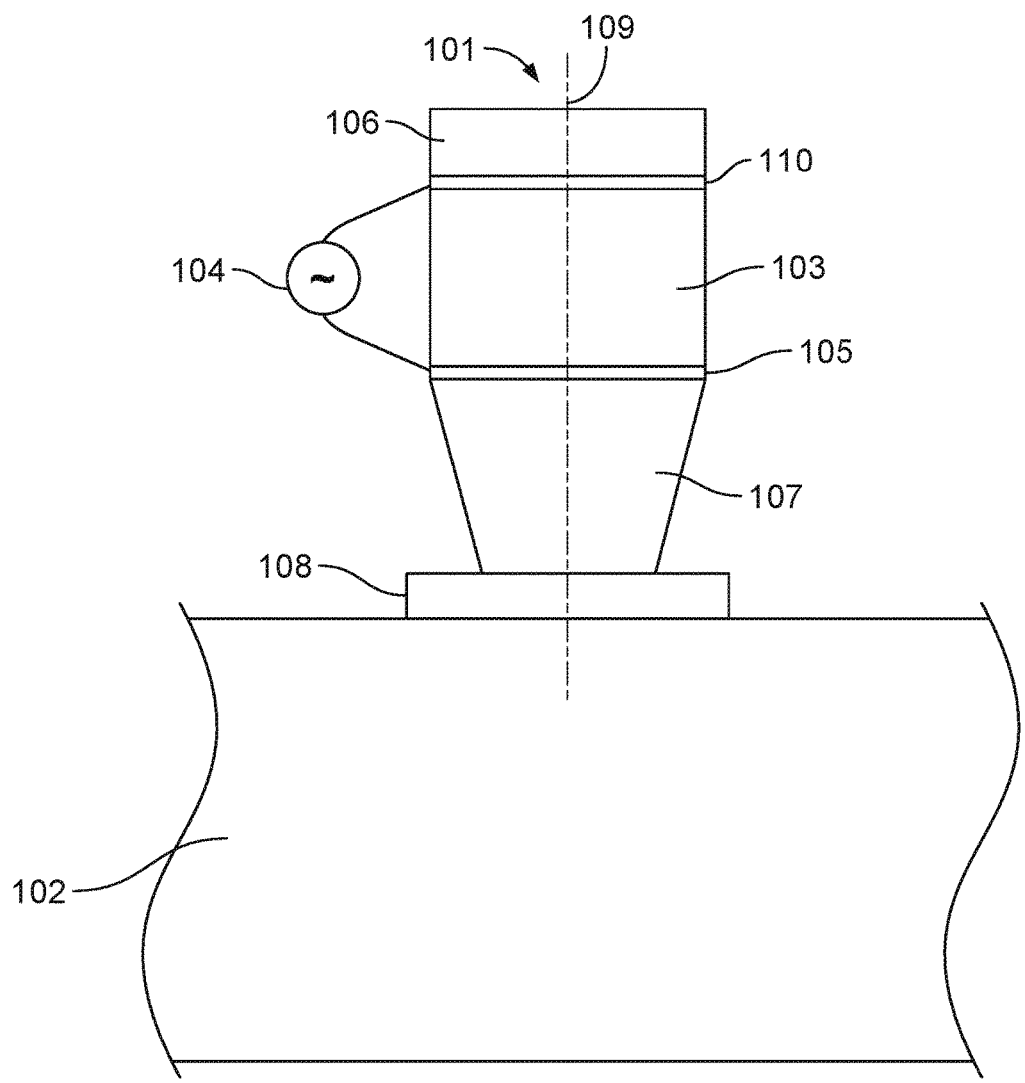
FIG. 1 is a schematic diagram illustrating an embodiment of an ultrasonic yield strength measurement tool disposed on a sample.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term "processor" refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

A system for determining a material property is disclosed. The system comprises a sensor and a processor. The sensor is for measuring a set of material responses corresponding to a set of ultrasonic excitations. The set of material responses includes measurements to enable determination of a peak response for each of the set of ultrasonic excitations. The set of ultrasonic excitations includes ultrasonic excitations at a plurality of amplitudes and at a plurality of frequencies. Each of the set of ultrasonic excitations is of a continuous wave type. The processor is for determining a material property using the peak responses for each of the set of ultrasonic excitations.

In some embodiments, a method for determining a material property comprises receiving a set of material responses corresponding to a set of ultrasonic excitations. The set of material responses are determined using measurements to determine a peak response for each of the set of ultrasonic excitations. For example, an indication is provided to generate an ultrasonic excitation at an amplitude and a frequency and a signal is received that is detected to measure a response. The frequency is set to a plurality of frequencies at the same amplitude and at each frequency of the set of frequencies the response is received. The amplitude is set to a next amplitude and again, for each of a set of frequencies, the response is received. This produces response for set of ultrasonic excitations, which includes ultrasonic excitations at a plurality of amplitudes and at a plurality of frequencies. Each of the set of ultrasonic excitations is of a continuous wave type. A material property is determined using the peak responses for each of the set of ultrasonic excitations.

Device Architecture

In some embodiments, a device for making non-destructive in-situ measurements of the elastic yield strength of a sample (e.g., a steel plate or pipeline wall) is disclosed. The device determines the yield strength of a specimen based on transducing ultrasonic waves within the medium and correlating quantifiable characteristics of the resulting frequency response to the intrinsic elastic nonlinearity of the material. The device comprises a transducer and a processor. In various embodiments, the device includes one or more electrodes, an acoustic termination, a horn, a flange, a collar, power electronics, signal processors, a memory, a user interface, or any other appropriate device component.

FIG. 1 is a schematic diagram illustrating an embodiment of an ultrasonic yield strength measurement tool positioned on sample. In the example shown, signal generator 104 provides a voltage excitation signal that is applied across electromechanical transducer 103 by means of electrode 105 and electrode 110. Electromechanical transducer 103 converts a voltage excitation signal into a mechanical vibrational motion substantially parallel to axis 109. Acoustic termination cap 106, electromechanical transducer 103 with electrode 105 and electrode 110, horn 107, flange 108 and sample 102 form a resonant cavity that supports at least one standing elastic wave mode. Flange 108 is used to transmit vibrational energy transmitted through horn 107 into sample 102. Horn 107 is configured to magnify the amplitude of a mechanical vibration within sample 102.

Figure 2:
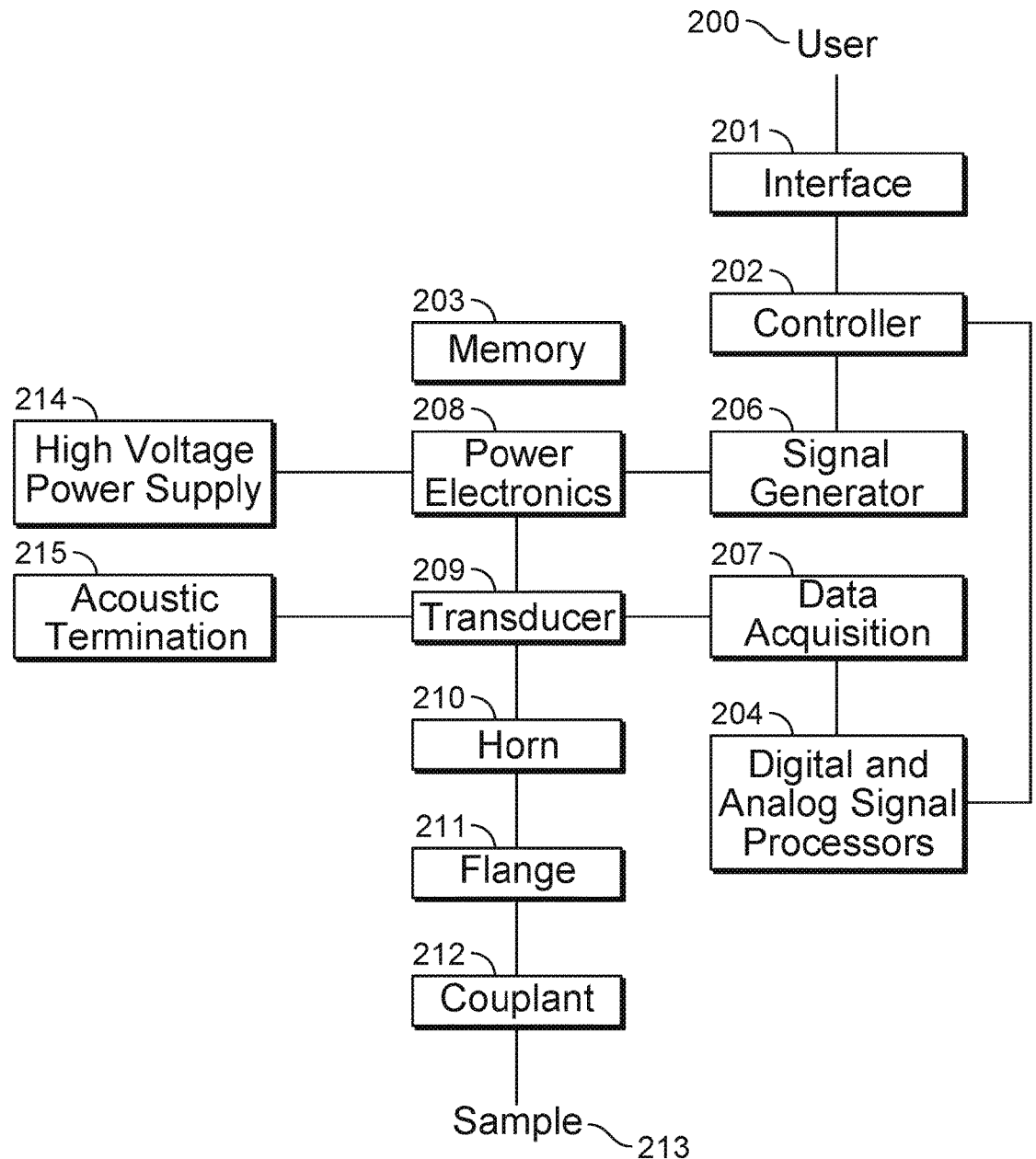
FIG. 2 is a block diagram illustrating an embodiment of the main components of an ultrasonic yield strength measurement tool.

FIG. 2 is a block diagram illustrating an embodiment of the overall system architecture for an embodiment of a yield strength measurement tool. Interface 201 provides user 200 an interface to receive indication from a user and to provide a user information. In various embodiments, a user interface includes a screen, a speaker, and indicator lights to display information, buttons, dials, a keyboard, a touchscreen to accept input, or any other appropriate user interface. Connected to interface 201 is controller 202 that executes programming stored on connected memory 203. Interface 201 sends commands to signal generator 206 and exchanges data with digital and analog signal processors 204. In some embodiments, controller 202 is implemented using a microcontroller or a personal computer. Memory 203 stores program instructions and measurement data. In various embodiments, memory 203 comprises one or more of the following: volatile storage, non-volatile storage, both volatile and non-volatile storage, or any other appropriate memory. Digital and analog signal processors 204 processes data using digital processing and/or analog signal processing (e.g., Fourier transforms, peak detection, analog-to-digital and digital-to-analog conversion, signal modulation and demodulation, comparators, algebraic functions, etc.). Signal generator 206 generates one or more excitation waveforms (e.g., a sinusoidal wave, square wave, sawtooth wave, impulse function, etc.) with one or more amplitudes and one or more frequencies prescribed by controller 202. The excitation waveform generated by signal generator 206 is amplified by power electronics 208. In some embodiments, power electronics 208 includes a power amplifier with a voltage gain in the range of 10 to 50 to drive transducer 209. Power electronics 208 is powered by high voltage power supply 214. In some embodiments, high voltage power supply 214 comprises a low electrical noise, direct current power supply that provides 0.1 to 2 A at +/−150 V. In various embodiments, high voltage power supply 214 is energized by an external source of electrical energy (e.g., a 120 V to 240 V alternating current wall socket), is energized by an onboard source of electrical energy (e.g., a battery), or any other appropriate power source. Transducer 209 converts an electrical excitation into a mechanical response (e.g., a piezoelectric element), and the resulting mechanical response into a corresponding electrical response. Transducer 209 connects to digital and analog signal processors 204 through data acquisition 207. In various embodiments, data acquisition 207 includes one or more of the following: a transimpedance amplifier, an attenuator, an oscilloscope, a voltmeter, an ammeter to sense transducer 209, or any other appropriate data acquisition components. Transducer 209 is acoustically coupled to acoustic termination 215 and horn 210. Acoustic termination 215 is used to tailor the strain profile of the mechanical response. In some embodiments, acoustic termination 215 is used to maximize the electro-mechanical conversion efficiency of transducer 209 (e.g., by positioning transducer 209 near a nodal plane of a resonant mode of vibration of the measurement instrument). Horn 210 focuses vibrational energy emitted from transducer 209 onto a smaller cross sectional area (e.g., to amplify the mechanical strain within sample 213). Sample 213 is connected to horn 210 by flange 211. Couplant 212 between flange 211 and sample 213 enhances the transmission of vibrational energy between the two parts. For example, transmission is enhanced by displacing air pockets (representing acoustic impedance discontinuities) that would scatter and/or reflect incident elastic waves. In various embodiments, flange 211 includes an acoustic reflector or an energy trap to mitigate losses associated with laterally propagating waves. Acoustic termination 215, transducer 209, horn 210, flange 211, couplant 212, and sample together represent the acoustically active portion of the yield strength measurement tool.

Theory of Operation

Figure 3A:
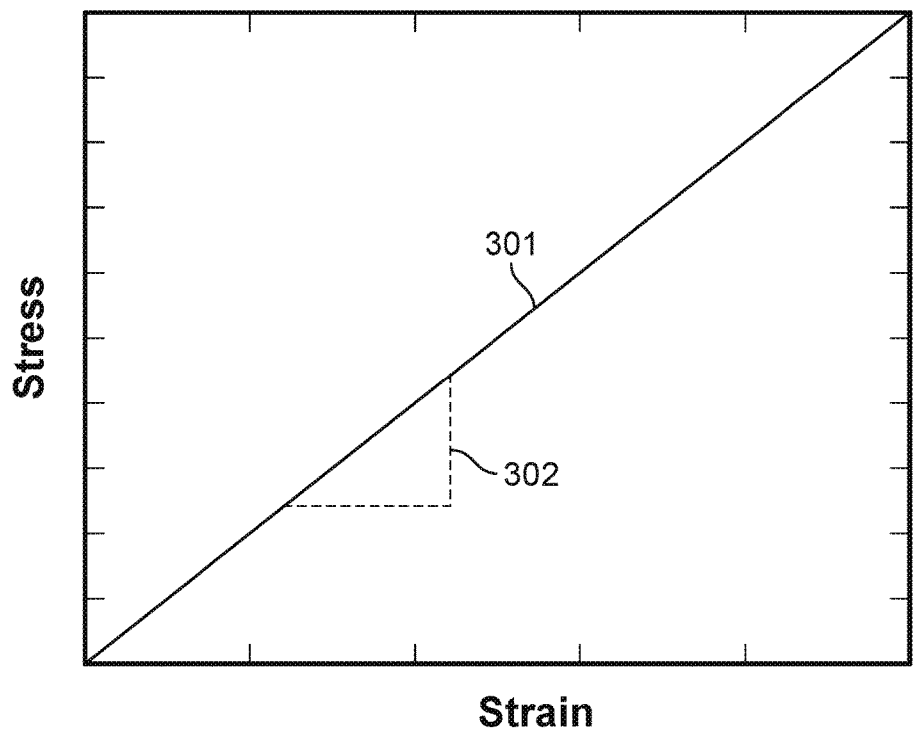
FIG. 3A is a graph illustrating an embodiment of the constitutive stress-strain behavior of a linearly-elastic material.

FIG. 3A is a graph illustrating an embodiment of a constitutive stress-strain behavior of a linearly-elastic material. In the example shown, the constitutive elastic behavior of an idealized elastic material is described by a linear relationship between a stress ($\sigma$) and a strain ($\epsilon$). Slope 302 of resulting stress-strain curve 301 is familiarly termed the Young's or stiffness modulus (E), which is defined by Equation 1.

$$\sigma = E\epsilon \qquad \text{Equation 1}$$

Although a Young's modulus is sometimes a property associated with an isotropic elastic material, it is also understood to apply more generally to a relevant effective stiffness property. For example, the Young's modulus or stiffness modulus may refer to a stiffness along a given direction in an anisotropic elastic material or to a piezoelectrically-stiffened stiffness in a piezoelectric material. The elastic constitutive behavior of an actual engineering material, such as steel, may appear substantially linear for small (typically less than 0.1%) values of strain magnitude, but exhibits substantially nonlinear behavior for larger values of strain magnitude. In some embodiments, the nonlinear stress-strain relationship is satisfactorily approximated for sufficiently small (typically around 0.2% for various metals) values of strain magnitude as a polynomial with first- and third-order terms.

Figure 3B:
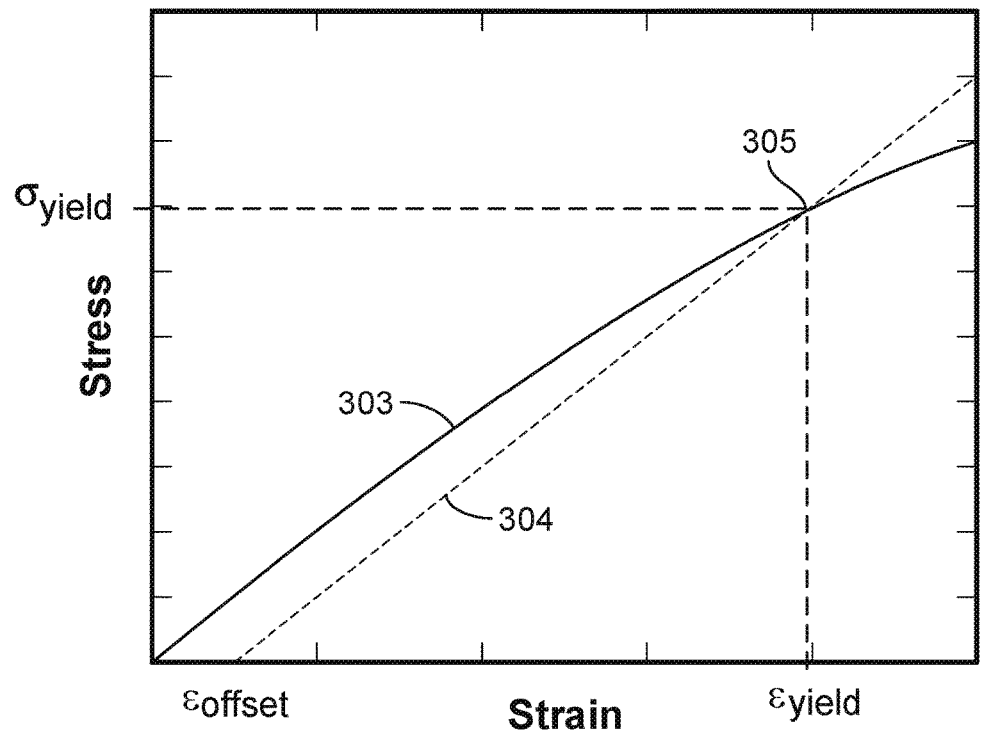
FIG. 3B is a graph illustrating an embodiment of the constitutive stress-strain behavior of a nonlinearly-elastic material.

FIG. 3B is a graph illustrating an embodiment of a constitutive stress-strain behavior of a nonlinearly-elastic material. In the example shown, to within a reasonable engineering approximation, the nonlinear constitutive behavior of an elastic medium is given by Equation 2 where $\alpha$ is the third-order stiffness coefficient.

$$\sigma = E\epsilon(1 + \alpha\epsilon^2) \qquad \text{Equation 2}$$

The working definition of yield strength is based on identifying intersection 305 of actual nonlinear stress-strain curve 303 and offset representation 304 of a material's linear elastic stiffness modulus given by Equation 3.

$$\sigma_{offset} = E(\epsilon - \epsilon_{offset}) \qquad \text{Equation 3}$$

Following some algebraic manipulation, the yield stress (or strength) can be determined in terms of the linear and nonlinear stiffness coefficients of the medium using Equation 4 where $\sigma_{yield}$ is yield stress or strength, and $\epsilon_{offset}$ is offset strain (typically ~0.2%).

$$\sigma_{yield} = E\left[\left(\frac{\epsilon_{offset}}{\alpha}\right)^{1/3} - \epsilon_{offset}\right] \qquad \text{Equation 4}$$

Thus, the problem is reduced to that of determining E and $\alpha$, which, according to the present device, are extracted from empirical observations of standing wave patterns or resonances that are induced within the medium by a transducer. A typical resonance of interest is in the range, for example, from 5 kHz to 250 kHz.

Figure 4A:
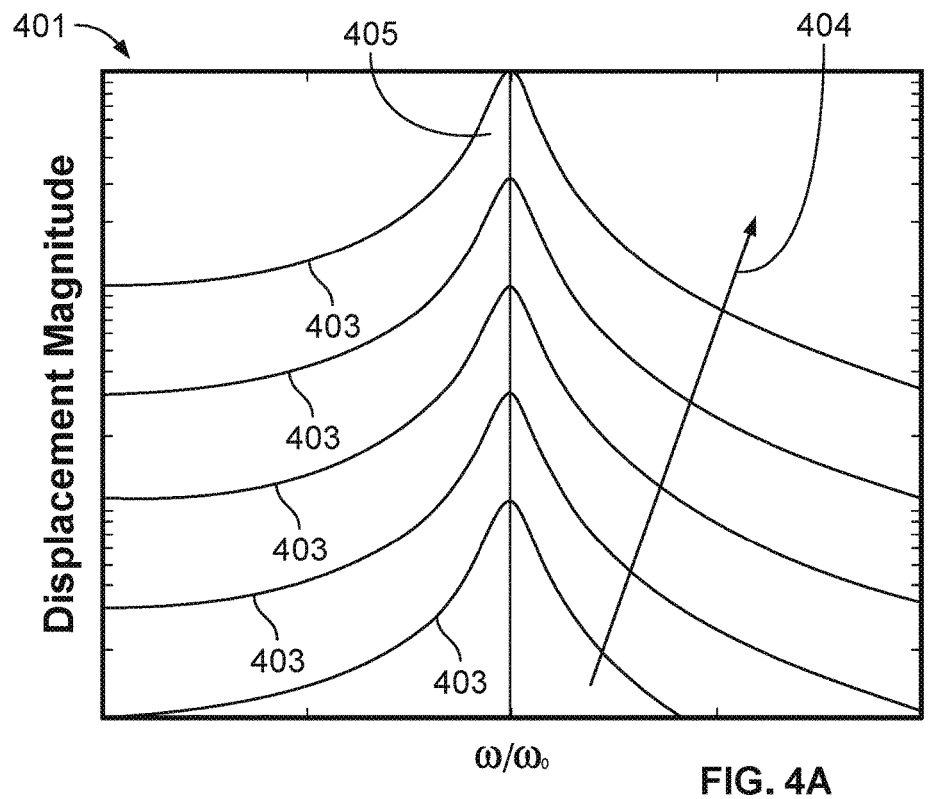
FIG. 4A is a graph illustrating an embodiment of the magnitude frequency response of a linear resonator.

FIG. 4A is a graph illustrating an embodiment of a magnitude frequency response of a linear resonator. In the example shown, graph 401 shows a displacement magnitude as a function of a normalized frequency ($\omega/\omega_0$). The displacement magnitudes or magnitude frequency responses 403 are shown for increasing values of an external forcing function (e.g., as indicated by 404). Magnitude frequency responses 403 exhibit substantially symmetric peaks about common nominal normalized resonant frequency 405.

Figure 4B:
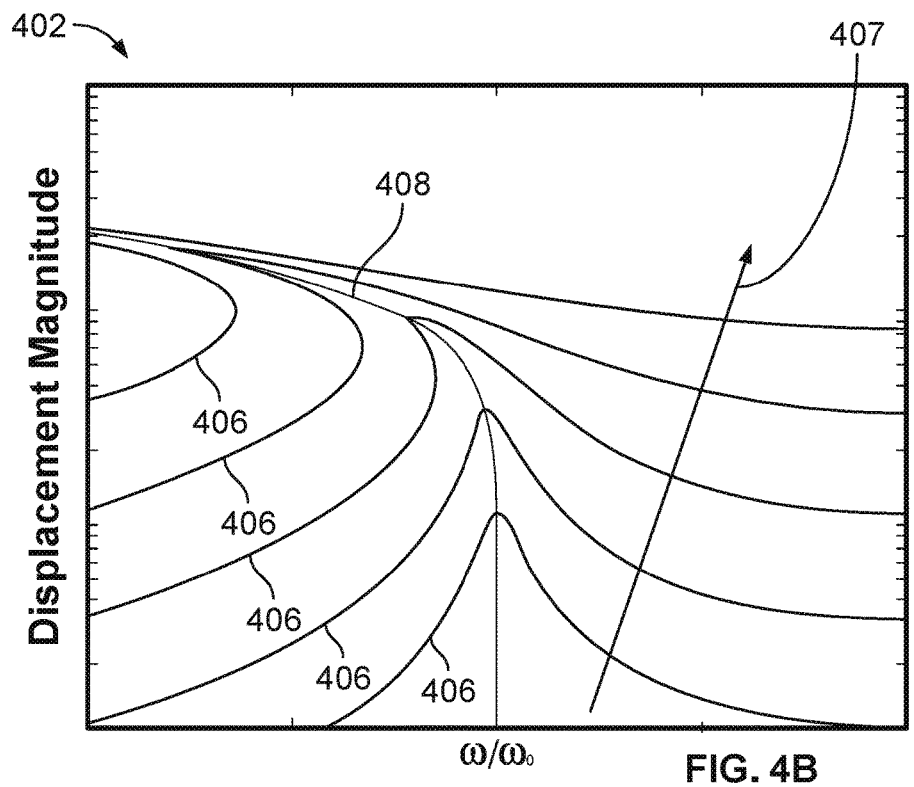
FIG. 4B is a graph illustrating an embodiment of the magnitude frequency response of a nonlinear resonator.

FIG. 4B is a graph illustrating an embodiment of a magnitude frequency response of a nonlinear resonator. In the example shown, graph 402 shows a displacement magnitude as a function of a normalized frequency ($\omega/\omega_0$). The displacement magnitudes or magnitude frequency responses 406 are shown for increasing values of an external forcing function (e.g., as indicated by 407). Magnitude frequency responses 406 exhibit substantially tilted peaks or "Duffing" behavior in proportion (for a given value of elastic nonlinearity $\alpha$) to the magnitude of an external forcing function. In this case, the frequency of maximum amplitude 408 decreases for increasing values of an external forcing function (i.e., the peaks tilt to the left); this behavior is representative of a system with a negative value of elastic nonlinearity $\alpha$ and is sometimes familiarly termed "spring softening."

In the absence of damping, the functional form of the observed locus of peak vibration amplitudes A($\omega$) is given by Equation 5.

$$A = \sqrt{\frac{4}{3\alpha}\left[\left(\frac{\omega}{\omega_0}\right)^2 - 1\right]} \quad \text{Equation 5}$$

The traveling and standing wave patterns are driven and sensed using ultrasonic transducer elements (e.g., as depicted in FIG. 1). The control volume for the measurement is substantially the projection of the transducer area through the wall thickness of the sample.

Figure 5:
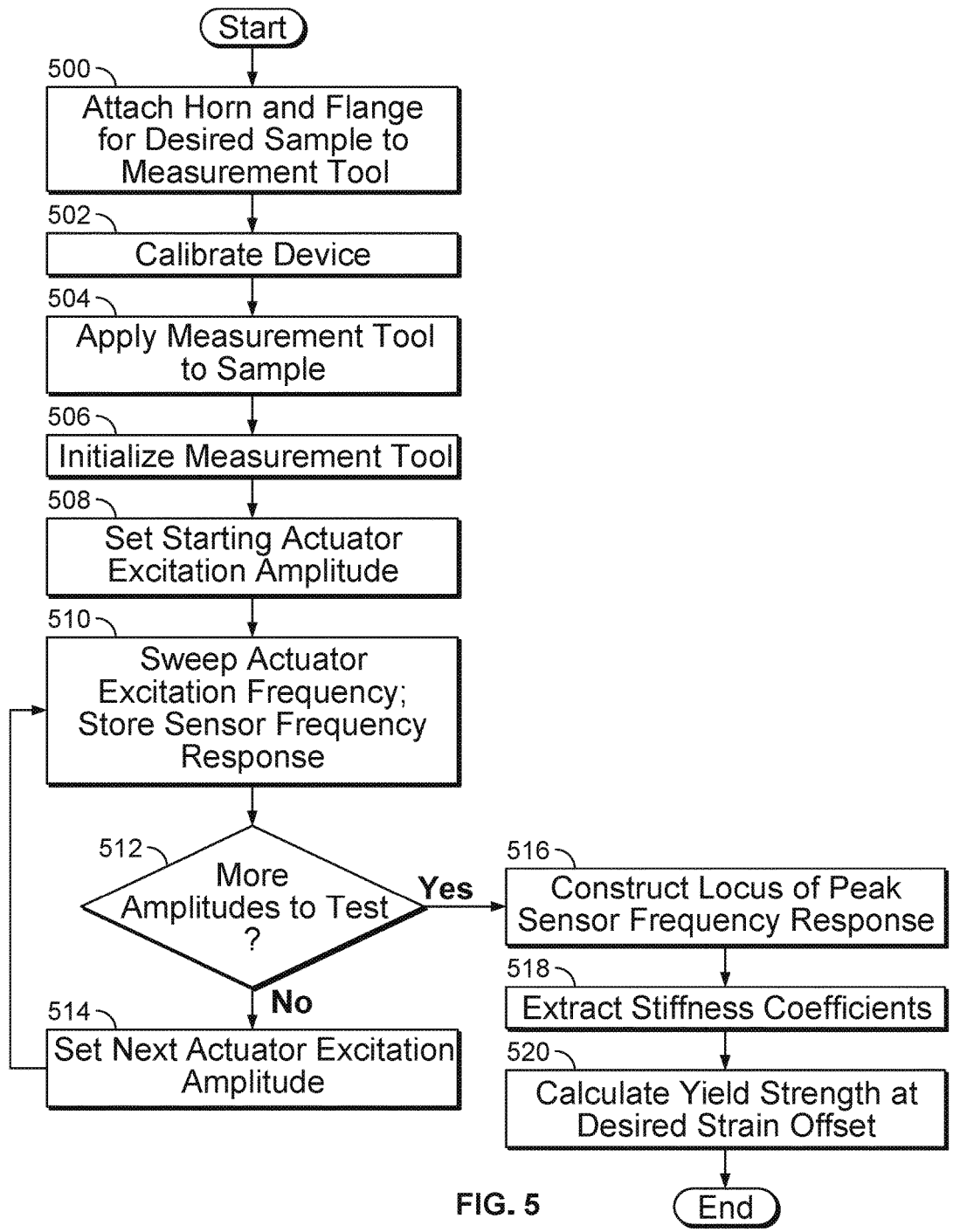
FIG. 5 is a flow diagram illustrating an embodiment of a process for determining the yield strength of a sample using an ultrasonic yield strength measurement tool.

FIG. 5 is a flow diagram illustrating an embodiment of a process for determining the yield strength of a sample using an ultrasonic yield strength measurement tool. In the example shown, in 500 a horn and a flange for the desired sample are attached to the measurement tool. For example, a horn and a flange are attached to the measurement tool that are appropriate for the desired sample. The horn is optimized for measuring samples of a certain thickness or range of thicknesses (e.g., by prescribing its axial length and radial profile); consequently, the measurement tool is configured with the appropriate horn based on the intended sample. Similarly, the flange is optimized to facilitate making yield strength measurements on samples of a specific geometry. For example, a flange for measuring flat samples (e.g., a plate) may itself have a flat end, and a flange for measuring cylindrical samples (e.g., a pipe) may itself have a curved end having the same radius of curvature as the sample. In 502, the measurement tool is calibrated. For example, a reference measurement in the absence of a sample establishes a baseline response to mitigate the effects of ambient temperature, transducer aging, and variations in the attachment of the horn and flange to the measurement tool. In 504, the measurement tool is applied to the sample. For example, the flange is placed on the outer wall of a pipe and secured in place (e.g., using a collar, screws or bolts, an adhesive, solder, brazing, welds, etc.). In 506, the measurement tool is initialized. For example, the processor and power supplies are powered up, input parameters are acquired from the user interface, coupling between the measurement instrument, and the sample is verified, and the natural frequency $f_n$ of interest is determined using ultrasonic measurements. In 508, a starting actuator excitation amplitude is set. For example, a linear response level voltage (e.g., a low voltage, a voltage relatively low compared to a voltage that elicits a nonlinear response from the material being tested, etc.) starting actuator excitation signal is applied. The starting actuator excitation signal is set to a small amplitude to elicit a substantially linear response. In 510, a sensor response is stored as the frequency of the actuator excitation is swept. For example, the frequency of a sinusoidal voltage waveform of the set amplitude is stepped over a range spanning from $0.95f_n$ to $1.05f_n$ and the amplitude and phase of the resulting output voltage waveform at each frequency step is stored in a memory. In 512, it is determined whether there are more actuator excitation amplitudes to test. For example, the determination analyzes whether the resulting output voltage waveform exhibits sufficient Duffing behavior to determine the underlying material nonlinearity and in the event it does not, it is indicated that there are more amplitudes to test, and in the event it does, it is indicated that there are not more amplitudes to test. In the event that there are more amplitudes to test, in 514, the actuator excitation amplitude is incremented and control passes to 510. In the event that there are not more amplitudes to test, in 516, a locus of peak sensor frequency response is constructed. For example, the locus of peak sensor frequency response is constructed by plotting the peak amplitude and corresponding frequency of each response waveform stored in memory in 510 on a common set of axes. In 518, stiffness coefficients are extracted. For example, the third order stiffness coefficient is determined by fitting (e.g., using a least-squares algorithm) a function of the form of Equation 5 to the measured locus of peak frequency response. In 520, yield strength is calculated at a desired strain offset. For example, the yield strength is calculated at a desired strain offset using Equation 4.

Figure 6A:
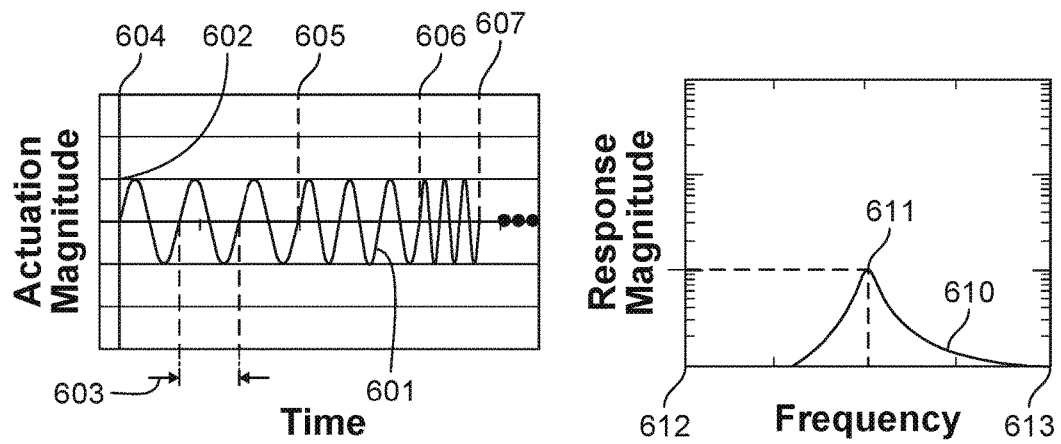
FIG. 6A is a pair of graphs illustrating an embodiment of a time domain representation of a first actuation signal and the resulting frequency domain representation of a first response signal of a nonlinear resonator.

FIG. 6A is a pair of graphs illustrating an embodiment of a time domain representation of a first actuation signal and the frequency domain representation of the resulting first response signal of a nonlinear resonator. In the example shown, excitation or actuation signal 601 having actuation magnitude 602 and first actuation period 603 (and corresponding frequency 612) is applied to an actuator. A response signal is measured as the frequency of an actuation signal is incremented from first frequency 612 to second frequency 613 to form frequency response 610. Frequency response 610 has peak response magnitude 611 occurring at ($f_1$, $X_1$). Each actuation signal is applied as a continuous waveform until the system substantially reaches steady-state, which may occur in a time interval roughly corresponding to $Q/f_{actuation}$, where Q is a quality factor of the overall resonant system. As examples, a first time interval spans from first time 604 to second time 605, a second time interval spans from second time 605 to third time 606, and a third time interval spans from third time 606 to fourth time 607.

Figure 6B:
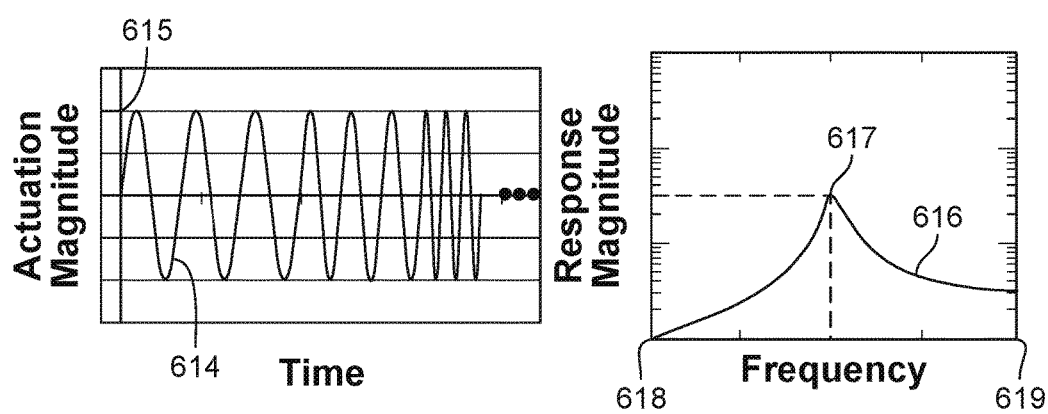
FIG. 6B is a pair of graphs illustrating an embodiment of a time domain representation of a second actuation signal and the resulting frequency domain representation of a second response signal of a nonlinear resonator.

FIG. 6B is a pair of graphs illustrating an embodiment of a time domain representation of a second actuation signal and the frequency domain representation of the resulting second response signal of a nonlinear resonator. In the example shown, excitation or actuation signal 614 having actuation magnitude 615, which is greater than actuation magnitude 602, is applied to an actuator. A response signal is measured as the frequency of an actuation signal is incremented from first frequency 618 to second frequency 619 to form frequency response 616. Frequency response 616 has a peak response magnitude 617 occurring at ($f_2$, $X_2$).

Figure 6C:
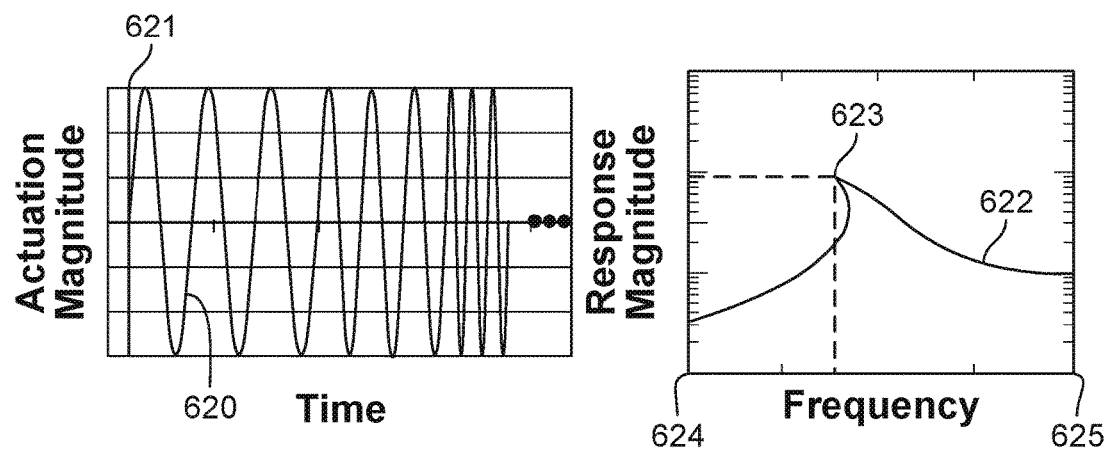
FIG. 6C is a pair of graphs illustrating an embodiment of a time domain representation of a third actuation signal and the resulting frequency domain representation of a third response signal of a nonlinear resonator.

FIG. 6C is a pair of graphs illustrating an embodiment of a time domain representation of a third actuation signal and the frequency domain representation of the resulting third response signal of a nonlinear resonator. In the example shown, excitation or actuation signal 620 having actuation magnitude 621, which is greater than actuation magnitude 615, is applied to an actuator. A response signal is measured as the frequency of an actuation signal is incremented from first frequency 624 to second frequency 625 to form frequency response 622. Frequency response 622 has a peak response magnitude 623 occurring at ($f_3$, $X_3$).

In some embodiments, the continuous wave type of excitation results in a system of forward and reverse propagating waves that interfere constructively in the vicinity of certain frequencies to cause standing wave modes or resonances. This approach using continuous wave type excitation differs fundamentally from non-destructive measurement approaches using measurements of the time of flight or scattering of ultrasonic wave pulses. In various embodiments, the number of actuation amplitudes or magnitudes applied in the course of making a measurement is between 3 and 20 or any other appropriate number. In various embodiments, the number of frequency steps applied at each actuation magnitude is between 10 and 1000 and spans a fractional bandwidth of approximately 2% to 40% where fractional bandwidth (BW %) is defined in Equation 6.

$$BW_\% = \frac{f_{High} - f_{Low}}{(f_{High} + f_{Low})/2} \quad \text{Equation 6}$$

Figure 7:
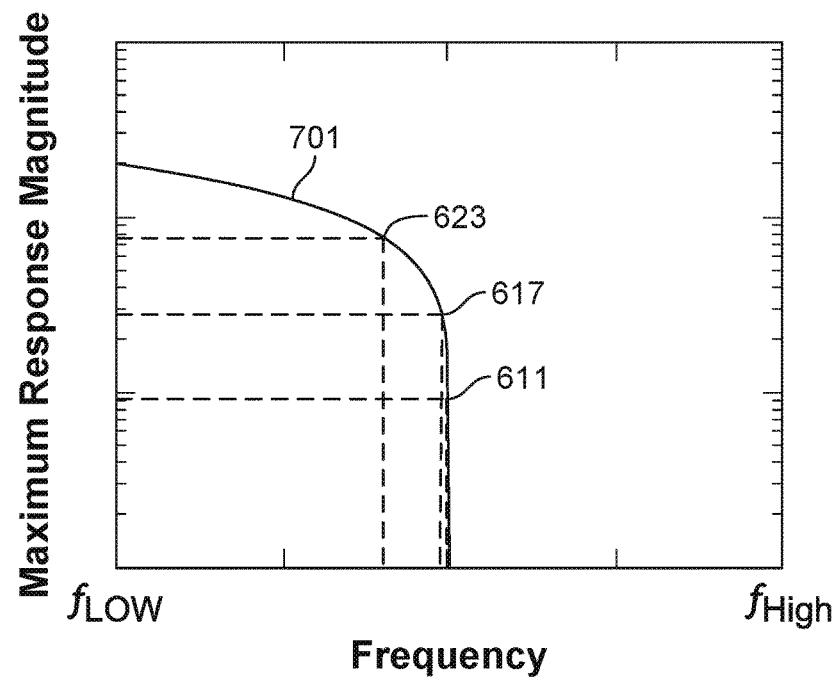
FIG. 7 is a graph illustrating an embodiment of the locus of maximum response magnitude of a nonlinear resonator.

FIG. 7 is a graph illustrating an embodiment of the locus of maximum response magnitude of a nonlinear resonator. In some embodiments, the locus of maximum response magnitude of a nonlinear resonator is described by Equation 5. In the example shown, each point along 701 corresponds to one peak response ($f_n$, $X_n$) measured at a particular actuation magnitude. For example, three points on 701 includes point 611 measured at amplitude 602, point 617 measured at amplitude 615, and point 623 measured at amplitude 621. The value of the third-order stiffness coefficient $\alpha$ is determined by fitting the ($f_n$, $X_n$) measurement data to the empirically-determined A($\omega$) by using a curve fitting technique (e.g., a least squares fit algorithm, etc.) implemented on a processor. Finally, the yield strength is calculated according to Equation 4, where the Young's modulus E is calculated from measurement data corresponding to a low magnitude actuation signal using the well-known relation for a wave propagation velocity $c_l$ given by Equation 7 or a transcendental frequency equation of the overall system.

$$c_l = \sqrt{E/\rho} \quad \text{Equation 7}$$

The mass density $\rho$ is assumed to be a standard value (e.g., approximately 7900 kg/m$^3$ for most steel alloys) with no substantial loss of overall measurement accuracy. In various embodiments, the frequency response measured by a sensor includes the magnitude, phase, or both of a physical quantity (e.g., a mechanical displacement, a mechanical velocity, an electrical impedance, an electrical voltage, an electrical current, an electrical charge, etc.). In various embodiments, the excitation applied by an actuator comprises a substantially continuous wave voltage, current, force, stress, or any other appropriate applied excitation.

Figure 8:
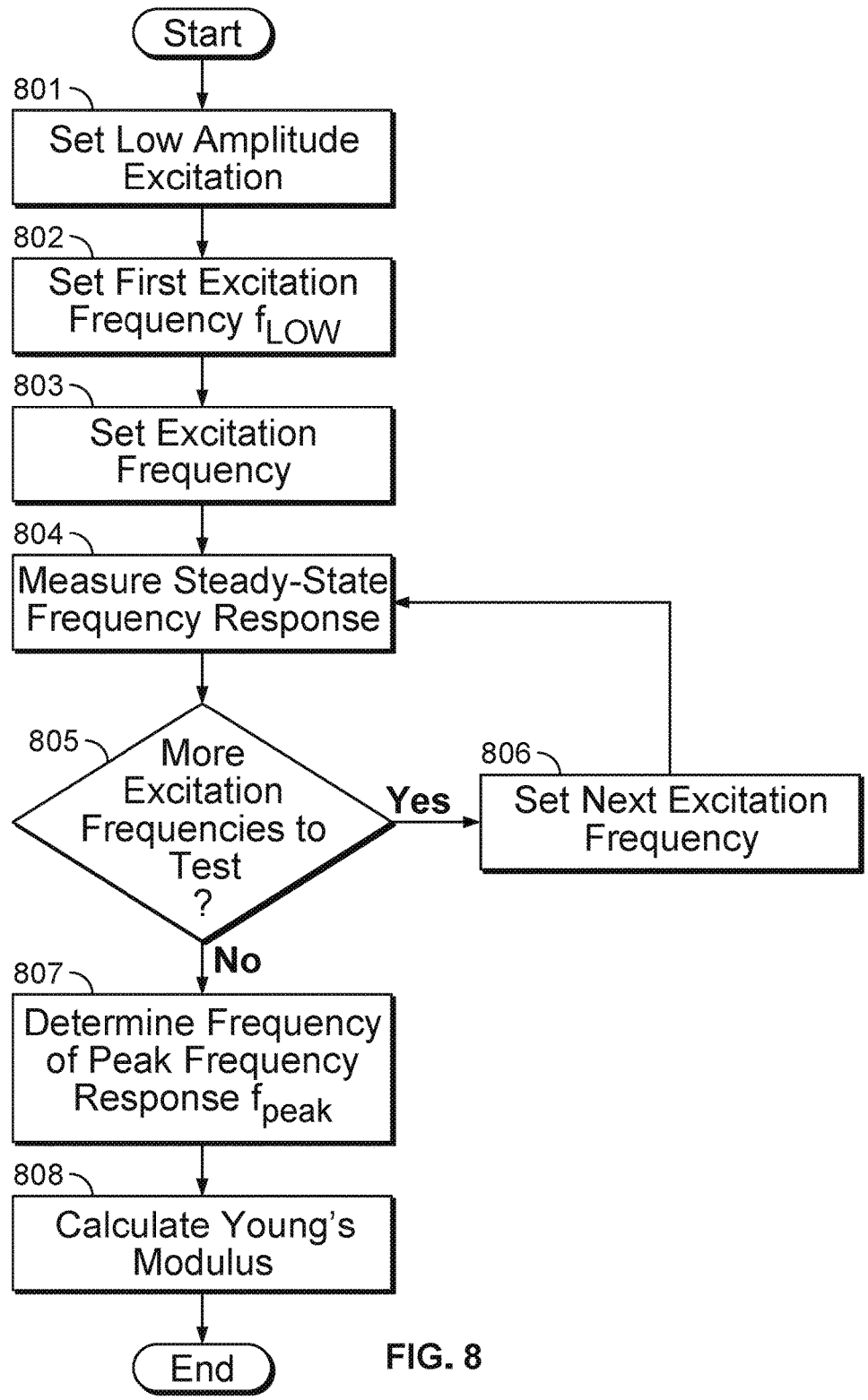
FIG. 8 is a flow diagram illustrating an embodiment of a process for determining the Young's modulus of a sample using an ultrasonic yield strength measurement tool.

FIG. 8 is a flow diagram illustrating an embodiment of a process for determining the Young's modulus of a sample using an ultrasonic yield strength measurement tool. In the example shown, in 801 a low amplitude excitation is set. For example, a low amplitude excitation is determined and applied to a transducer. The amplitude of the excitation waveform (e.g., sinusoid, square wave, sawtooth wave, impulse function, etc.) is sufficiently low that the effects of the material nonlinearity of the sample do not manifest in the resulting frequency response. In 802, a first excitation frequency $f_{LOW}$ is set. For example, the first excitation frequency is in the range of 80% to 99% of the natural frequency of interest (i.e., $0.8f_n < f_{LOW} < 0.99f_n$). In 804, the steady-state frequency response is measured. For example, the amplitude and phase, the real and imaginary parts, and/or Smith Chart representation of a response voltage waveform are measured. In 805, it is determined whether there are more excitation frequencies to test. In the event that there are more frequencies to test, in 806, the next excitation frequency is set and control passes to 804. For example, the excitation frequency is incremented by an amount ranging from ($f_{HIGH} - f_{LOW}$)/1000 to ($f_{HIGH} - f_{LOW}$)/100 where the final excitation frequency $f_{HIGH}$ is in the range of 101% to 120% of the natural frequency of interest (i.e., $1.01f_n < f_{HIGH} < 1.2f_n$). In various embodiments, the frequency is incremented logarithmically—for example, at a rate of 10 to 1000 points per decade. In some embodiments, the frequency is decremented from $f_{HIGH}$ to $f_{LOW}$. In the event that there are not more frequencies to test, in 807, the frequency $f_{peak}$ of the maximum amplitude of the resulting frequency response eak is determined. For example, with low amplitude excitation, the frequency at which the response voltage waveform assumes its maximum value substantially corresponds to the natural frequency of the induced mode of vibration. In 808, the Young's modulus is calculated. For example, the Young's modulus of the sample is calculated using the frequency equation for the corresponding linear mode of vibration.

Figure 9:
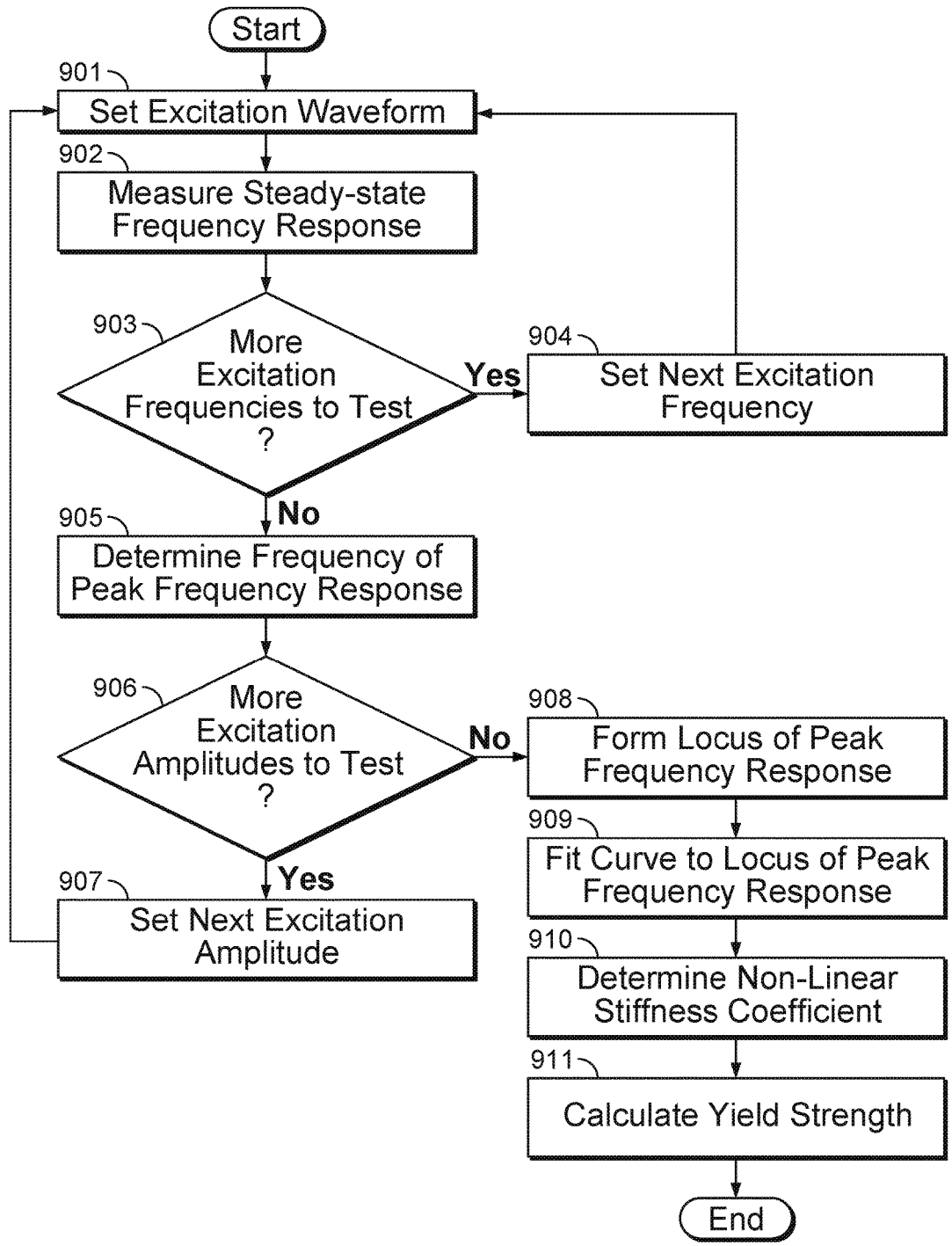
FIG. 9 is a flow diagram illustrating an embodiment of a process for determining the yield strength of a sample using an ultrasonic yield strength measurement tool.

FIG. 9 is a flow diagram illustrating an embodiment of a process for determining the yield strength of a sample using an ultrasonic yield strength measurement tool. In the example shown, in 901 an excitation waveform is set. For example, an excitation waveform is determined and an indication is sent to apply a signal to a transducer that achieves the desired excitation. In some embodiments, the first excitation signal is a voltage waveform (e.g., sinusoid, square wave, sawtooth wave, impulse function, etc.) having sufficiently low amplitude that the effects of the material nonlinearity of the sample do not manifest in the resulting frequency response and a frequency in the range of 80% to 99% of the natural frequency of interest. In 902, the resulting steady-state frequency response of the system is measured. For example, a measurement of the frequency response is made after the system reaches steady-state. The time interval between applying the excitation waveform and reaching steady-state is reached is approximately Q/$f_n$ where Q is the resonant quality factor of the system and $f_n$ is the natural frequency of interest. In various embodiments, the response is measured as a magnitude and phase, real and imaginary part, or any other appropriate representation of a complex quantity for the response. In 903, it is determined whether there are more excitation frequencies to test. In the event that there are more frequencies to test, in 904, the next excitation frequency is set and control passes to 901. For example, the excitation frequency is incremented by an amount ranging from ($f_{HIGH} - f_{LOW}$/1000 to ($f_{HIGH} - f_{LOW}$)/100 where the final excitation frequency $f_{HIGH}$ is in the range of 101% to 120% of the natural frequency of interest (i.e., $1.01f_n < f_{HIGH} < 1.2f_n$). In various embodiments, the frequency is incremented logarithmically at a rate of 10 to 1000 points per decade, or at any other appropriate increment. In some embodiments, the frequency is decremented from $f_{HIGH}$ to $f_{LOW}$. In the event that there are not more frequencies to test, in 905, the frequency $f_{peak}$ of the peak amplitude of the resulting frequency response is determined. For example, the maximum point of the frequency response is determined and the corresponding associated frequency is stored in memory. In 906, it is determined whether there are more excitation amplitudes to test. In the event that there are more amplitudes to test, in 907, the excitation amplitude is set and control passes to 901. For example, the excitation amplitude is incremented by an amount ranging from $(A_{HIGH}-A_{LOW})/100$ to $(A_{HIGH}-A_{LOW})/5$ where the final excitation amplitude $A_{HIGH}$ is in the range results in a maximum stress intensity within the sample in the range of 10% to 90% of its yield strength. In various embodiments, the amplitude is incremented logarithmically at a rate of 1 to 10 points per decade, or at any other appropriate increment. In some embodiments, the amplitude is decremented from $A_{HIGH}$ to $A_{LOW}$. In the event that there are not more amplitudes to test, in 908, a locus of peak sensor frequency response is formed. For example, the locus of peak sensor frequency response is formed or constructed by plotting the peak amplitude and corresponding frequency of each response waveform measured in 905 on a common set of axes. In 909, the locus of peak frequency response is fitted to a curve. For example, a least-squares algorithm is used to fit a function of the form of Equation 5 to the measured frequency response locus. The least-squares fit provides an estimate of the nonlinear stiffness coefficient and from this the Young's modulus is determined (e.g., as described in detail above). In 911, the yield strength is calculated. For example, the yield strength is calculated at a desired strain offset (e.g., using Equation 4).

Transduction Schemes

In some embodiments, a transducer comprises a sensor that converts a physical quantity into an electrical signal or an actuator that converts an electrical signal into a physical quantity. In various embodiments, physical quantities that are transduced include strain, stress, force, displacement, velocity, temperature, light (e.g., infrared, visible, ultraviolet, X-ray, etc.), magnetic flux, or any other appropriate physical quantity. In various embodiments, a sensing scheme uses piezoelectrics, electrostatics, optics, pyroelectrics, piezoresistivity, or any other appropriate sensing scheme. In various embodiments, an actuation scheme uses a piezoelectric actuation, a magnetostrictive actuation, an electrostrictive actuation, an electrostatic actuation, a thermal actuation, a mechanical striker actuation, or any other appropriate actuation. In various embodiments, the same physical element is used for sensing and actuation (e.g., a single piezoelectric transducer acts as a sensor using the direct piezoelectric effect and as an actuator using the inverse piezoelectric effect); such an arrangement provides the basis for a one-port transduction scheme. In some embodiments, separate elements are used for sensing and actuation; such an arrangement provides the basis for a two-port transduction scheme. In some embodiments, a device using a two-port transduction scheme uses the same modality for both sensing and actuation (e.g., piezoelectric sensing and piezoelectric actuation). In some embodiments, a device using a two-port transduction scheme uses different modalities for sensing and actuation (e.g., magnetostrictive actuation and optical sensing).

Piezoelectric Material

In some embodiments, a piezoelectric material is characterized by an intrinsic constitutive behavior whereby an applied or induced mechanical stress or strain is converted into an electrical signal and an applied or induced electrical signal is converted into a mechanical stress or strain. In some embodiments, a piezoelectric material comprises lead zirconate titanate (PZT). In some embodiments, a PZT piezoelectric material is formed by sintering a PZT powder followed by a polling process. In some embodiments, a polling process involves subjecting a piezoelectric material to an elevated temperature and applying an external electric field along a polling axis while returning the material to ambient temperature. In some embodiments, a polling process is used to impart the requisite asymmetry in the crystal structure of a piezoelectric material to bestow the desired piezoelectric properties.

Piezoelectric Transducer

Figure 10:
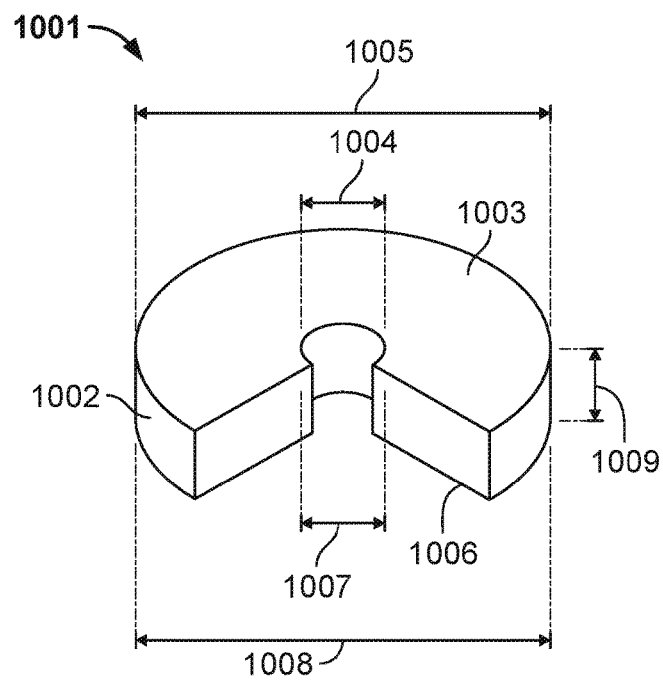
FIG. 10 is a diagram illustrating an embodiment of a cutaway view of an annular electromechanical transducer.

FIG. 10 is a diagram illustrating an embodiment of a cutaway view of an annular electromechanical transducer. Piezoelectric transducer 1001 is formed using piezoelectric layer 1002 and has first end 1003 with first inner diameter 1004 and first outer diameter 1005, and second end 1006, parallel to a first end, with second inner diameter 1007 and second outer diameter 1008. First end 1003 and second end 1006 are separated by thickness 1009. In various embodiments, first inner diameter 1004 and second inner diameter 1007 are zero (corresponding to a disk transducer), are non-zero (corresponding to an annular transducer), are the same, are different, or any other appropriate dimension. In various embodiments, first outer diameter 1005 and second outer diameter 1008 are substantially equal (corresponding to a cylindrical transducer), or are not equal (corresponding to a tapered transducer). In some embodiments, a piezoelectric transducer includes a first electrode proximate to a first end and a second electrode proximate to a second end. Typical values for an inner and outer diameter of a piezoelectric transducer are, for example, 0 to 10 mm and 5 to 30 mm, respectively. Typical values for a thickness of a piezoelectric transducer are, for example, 0.5 to 10 mm.

Figure 11:
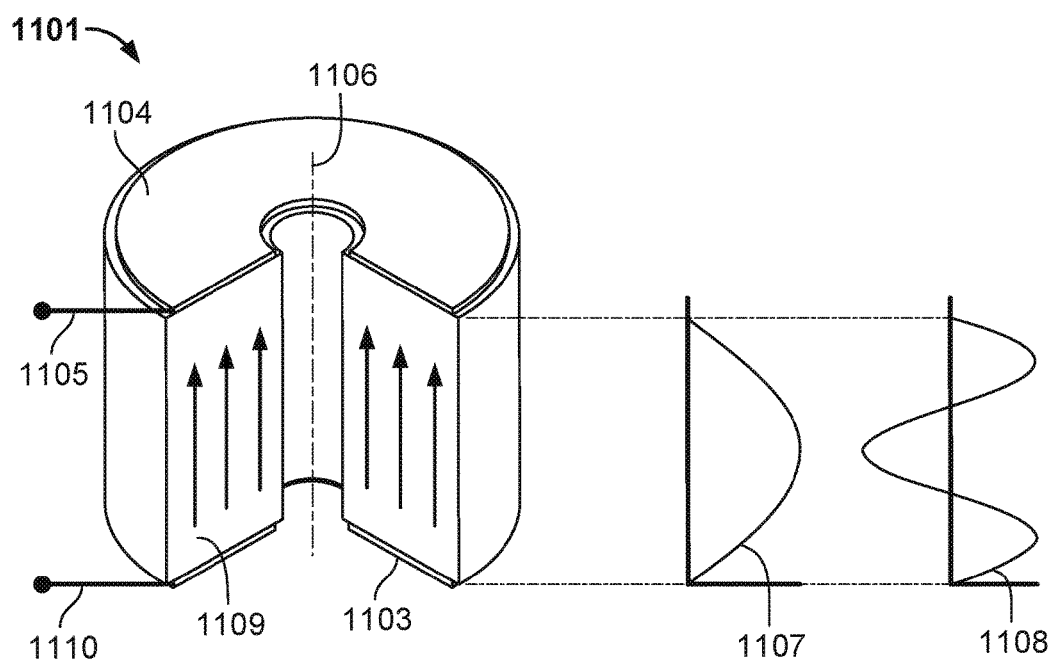
FIG. 11 is a diagram illustrating an embodiment of a cutaway view of an annular electromechanical transducer configured to support one-port operation.

FIG. 11 is a diagram illustrating an embodiment of a cutaway view of an annular electromechanical transducer configured to support one-port operation. In the example shown, an electric field, which is transduced into a mechanical strain by the inverse piezoelectric effect, is created within piezoelectric transducer 1101 by applying a potential difference between first electrode 1103 and second electrode 1104. In various embodiments, electrode 1103 or electrode 1104 each include one or more leads (e.g., lead 1105 and lead 1110 to facilitate applying an electrical potential and/or current. In the event that an applied potential difference is a time varying potential difference that contains a frequency that substantially corresponds to a mechanical resonance of a transducer system (including any elements such as an acoustic termination, horn, flange, or sample that it is connected to), the resulting strain is magnified in proportion to an effective resonant quality factor (Q) of the system. A mechanical strain is in turn transduced by the direct piezoelectric effect into an electric field that creates a first piezoelectric charge on a first electrode and a second piezoelectric charge on a second electrode. In some embodiments, an annular piezoelectric transducer supports vibrational modes that are characterized by axial displacement substantially parallel to axis 1106. As an example, piezoelectric transducer 1101 couples with a fundamental axial extensional mode of vibration having axial strain profile 1107 and with a third axial extensional mode of vibration having axial strain profile 1108. In some embodiments, polling direction 1109 of a piezoelectric material is substantially parallel to axis 1106.

Figure 12:
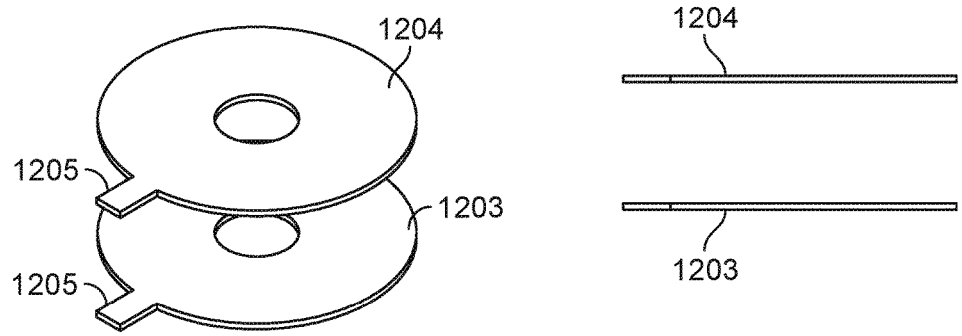
FIG. 12 are diagrams illustrating an embodiment of isometric and side views of electrodes.

FIG. 12 is a diagram illustrating an embodiment of isometric and side views of an electrode. In the example shown, first electrode 1203 and second electrode 1204 have leads 1205 that are used to support one-port operation of a piezoelectric transducer (e.g., piezoelectric transducer 1101 of FIG. 11). Leads 1205 are formed either using the same material as an electrode or as a separate element (e.g., a length of conductive wire) that are subsequently joined to one or more electrodes (e.g., using a solder, brazing, or conductive epoxy based process). In various embodiments, an electrode or a lead is formed using an electrically conductive material, where the conductive material comprises a metal including one or more of the following: beryllium copper, aluminum, copper, nickel, molybdenum, tungsten, ruthenium, or any other appropriate conductive material. Typical values for the thickness of an electrode or lead are 10 um to 1 mm.

Stacked Piezoelectric Transducer

In some embodiments, a stacked piezoelectric transducer comprises two or more piezoelectric transducer disks, annuli, tapers or combinations thereof arranged along a substantially common axial axis—for example with a second end of a first piezoelectric transducer proximate to a first end of a second piezoelectric transducer. In various embodiments, a stacked piezoelectric transducer has every piezoelectric transducer layer with a polling direction that points in substantially the same direction along a substantially common axial axis, has at least one transducer layer with a polling direction that points in substantially the opposite direction along a substantially common axial axis as another transducer layer, or any other appropriate configuration of polling directions with a stacked piezoelectric transducer. In some embodiments, adjacent piezoelectric transducer layers in a stacked piezoelectric transducer share a common electrode. In various embodiments, one or more electrical interconnects are formed between an electrode, an external voltage source (e.g., a signal generator) or sink (e.g., a signal analyzer or ground) or another electrode. In some embodiments, one or more electrodes are also allowed to float electrically.

Figure 13:
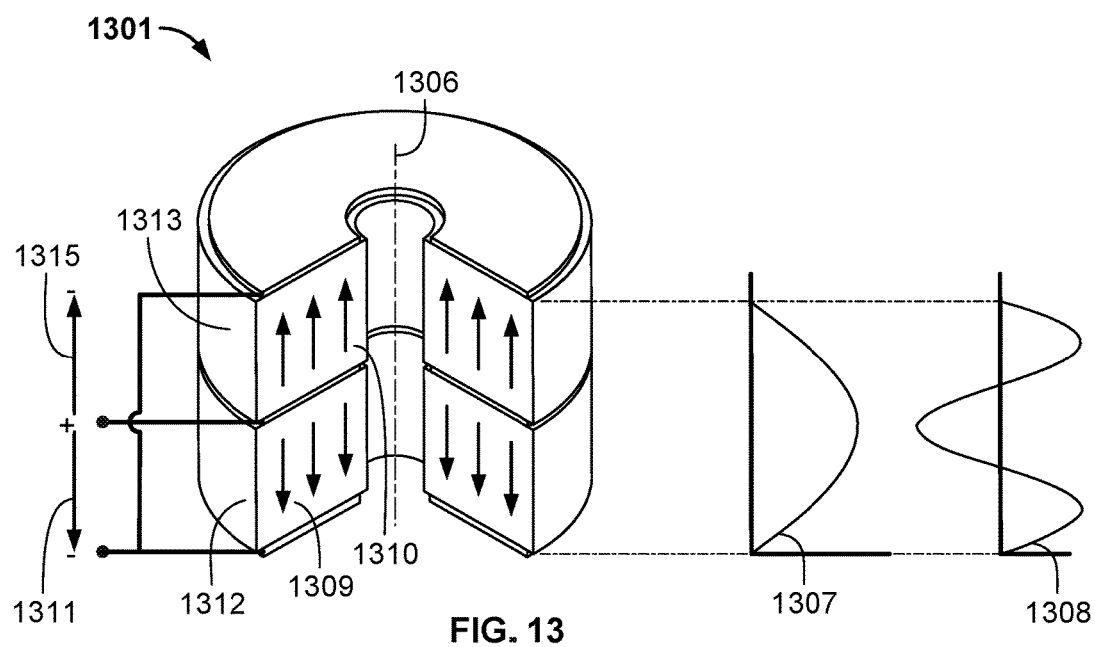
FIG. 13 is a diagram illustrating an embodiment of a cutaway view of a stacked piezoelectric transducer with two annular transducer layers configured for one-port operation having piezoelectric polling directions alternating between adjacent layers.

FIG. 13 is a diagram illustrating an embodiment of a cutaway view of a stacked piezoelectric transducer with two annular transducer layers configured for one-port operation having piezoelectric polling directions alternating between adjacent layers. In the example shown, first piezoelectric polling direction 1309 within first piezoelectric layer 1312 and second piezoelectric polling direction 1310 within second piezoelectric layer 1313 are pointing in substantially the same direction as applied electric field 1311 and electric field 1315, respectively. When the frequency of time-varying applied electric field 1311 and electric field 1315 correspond to the frequency of an axial mode of vibration of stacked transducer 1301, the stacked transducer operates preferentially in an odd numbered axial extensional mode (e.g., first axial extensional mode 1307 or third axial extensional mode 1308) about axis 1306.

Figure 14:
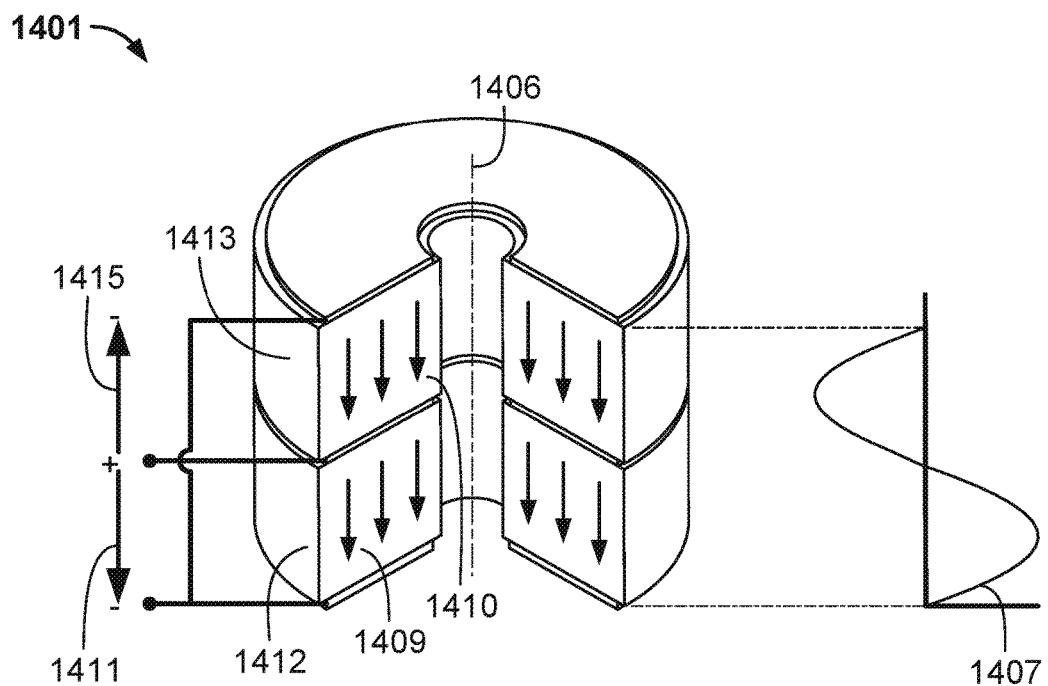
FIG. 14 is a diagram illustrating an embodiment of a cutaway view of a stacked piezoelectric transducer with two annular transducer layers configured for one-port operation having piezoelectric polling directions aligned between adjacent layers.

FIG. 14 is a diagram illustrating an embodiment of a cutaway view of a stacked piezoelectric transducer with two annular transducer layers configured for one-port operation having piezoelectric polling directions aligned between adjacent layers. In the example shown, first piezoelectric polling direction 1409 points in substantially the same direction as applied electric field 1411 within first piezoelectric layer 1412. Second piezoelectric polling direction 1410 points in substantially the opposite direction as applied electric field 1415 within second piezoelectric layer 1413. When the frequency of time-varying applied electric field 1411 and electric field 1415 correspond to the frequency of an axial mode of vibration of stacked transducer 1401, stacked transducer 1401 operates preferentially in an even numbered axial extensional mode (e.g., second axial extensional mode 1407 or a sixth axial extensional mode) about axis 1406.

Figure 15:
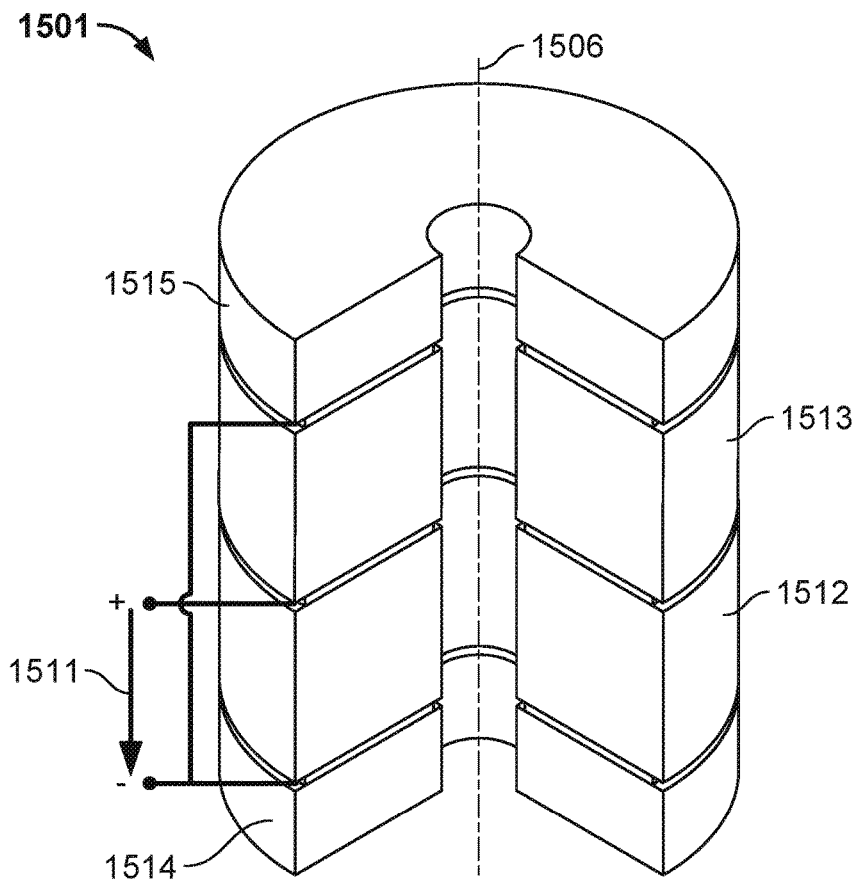
FIG. 15 is a diagram illustrating an embodiment of a cutaway view of a stacked piezoelectric transducer with two annular transducer layers configured for one-port operation having coaxial insulating layers.

FIG. 15 is a diagram illustrating an embodiment of a cutaway view of a stacked piezoelectric transducer with two annular transducer layers configured for one-port operation having coaxial insulating layers. In the example shown, first coaxial insulating layer 1514 is proximate to first piezoelectric layer 1512, and second coaxial insulating layer 1515 is proximate to second piezoelectric layer 1513. In various embodiments, first piezoelectric layer 1512 has the same piezoelectric polarization direction as second piezoelectric layer 1513, or first piezoelectric layer 1512 has the opposite piezoelectric polarization direction as second piezoelectric layer 1513. When the frequency of time-varying applied electric field 1511 corresponds to the frequency of an axial mode of vibration of stacked transducer 1501, stacked transducer 1501 operates preferentially in a corresponding axial extensional mode of vibration about axis 1506.

Figure 16:
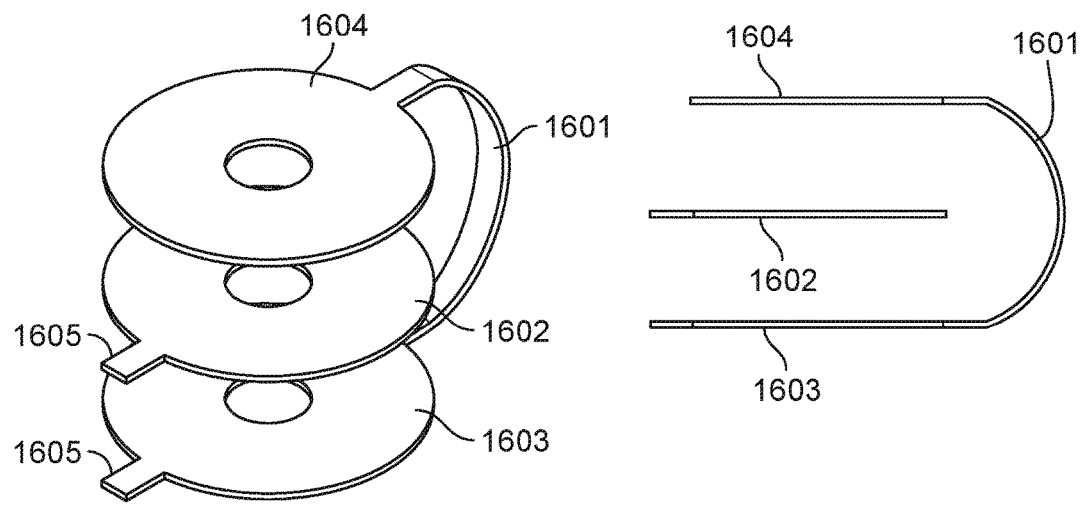
FIG. 16 is a diagram illustrating an embodiment of isometric and side views of an electrode scheme that is used to support one-port operation of a stacked transducer with two transducer layers.

FIG. 16 is a diagram illustrating an embodiment of isometric and side views of an electrode scheme that is used to support one-port operation of a stacked transducer with two transducer layers. In some embodiments, the electrodes are used with a stacked piezoelectric transducer with two annular transducer layers (e.g., stacked piezoelectric transducer 1301 of FIG. 13, stacked piezoelectric transducer 1401 of FIG. 14, or stacked piezoelectric transducer 1501 of FIG. 15). In the example shown, first electrode 1603 and third electrode 1602 include leads 1605 to facilitate forming electrical connections with various components. Second electrode 1604 is connected to first electrode 1603 by means of connector 1601. Connector 1601 is formed either using the same material as an electrode or as a separate element (e.g., a length of conductive wire), and subsequently joined to one or more electrodes (e.g., using a solder, brazing, or conductive epoxy based process). In various embodiments, an electrode, a lead, or a connector is formed using an electrically conductive material using one or more of the following metals: beryllium copper, aluminum, copper, nickel, molybdenum, tungsten, ruthenium, or any other appropriate metal. A typical value for the thickness of an electrode or connector is between 10 μm to 1 mm.

Figure 17:
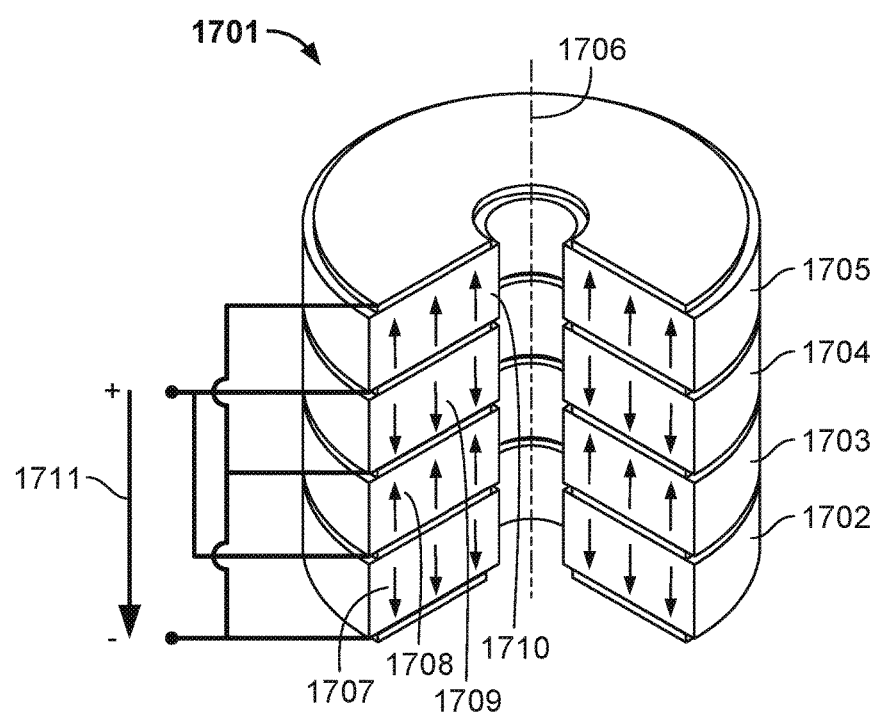
FIG. 17 is a diagram illustrating an embodiment of a cutaway view of a stacked piezoelectric transducer with four annular transducer layers configured for one-port operation having piezoelectric polling directions alternating between adjacent layers.

FIG. 17 is a diagram illustrating an embodiment of a cutaway view of a stacked piezoelectric transducer with four annular transducer layers configured for one-port operation having piezoelectric polling directions alternating between adjacent layers. In the example shown, first piezoelectric polling direction 1707 points in substantially the same direction as applied electric field 1711 within first piezoelectric layer 1702, second piezoelectric polling direction 1708 points in substantially the same direction as applied electric field 1711 within second piezoelectric layer 1703, third piezoelectric polling direction 1709 points in substantially the same direction as applied electric field 1711 within third piezoelectric layer 1704, and fourth piezoelectric polling direction 1710 points in substantially the same direction as applied electric field 1711 within fourth piezoelectric layer 1705. When the frequency of time-varying applied electric field 1711 corresponds to the frequency of an axial mode of vibration of stacked transducer 1701, stacked transducer 1701 operates preferentially in an odd numbered axial extensional mode (e.g., a first axial extensional mode or a third axial extensional mode) about axis 1706.

In various embodiments, although not depicted explicitly in a figure, it is understood that more than four layers, each having a polling direction pointing in the same direction as an applied electric field may be stacked, and that such a transducer stack may operate preferentially in a corresponding fundamental axial extensional mode of the resulting overall stack. For example, a stacked transducer with six transducer layers preferentially operates in a fundamental axial extensional mode of the overall stack. The number of layers in a transducer stack is chosen, for example, to scale the electrical impedance of the transducer stack, to scale one or more natural frequencies of the transducer stack, or to scale the required voltage amplitude to achieve a given actuation effort.

Figure 18:
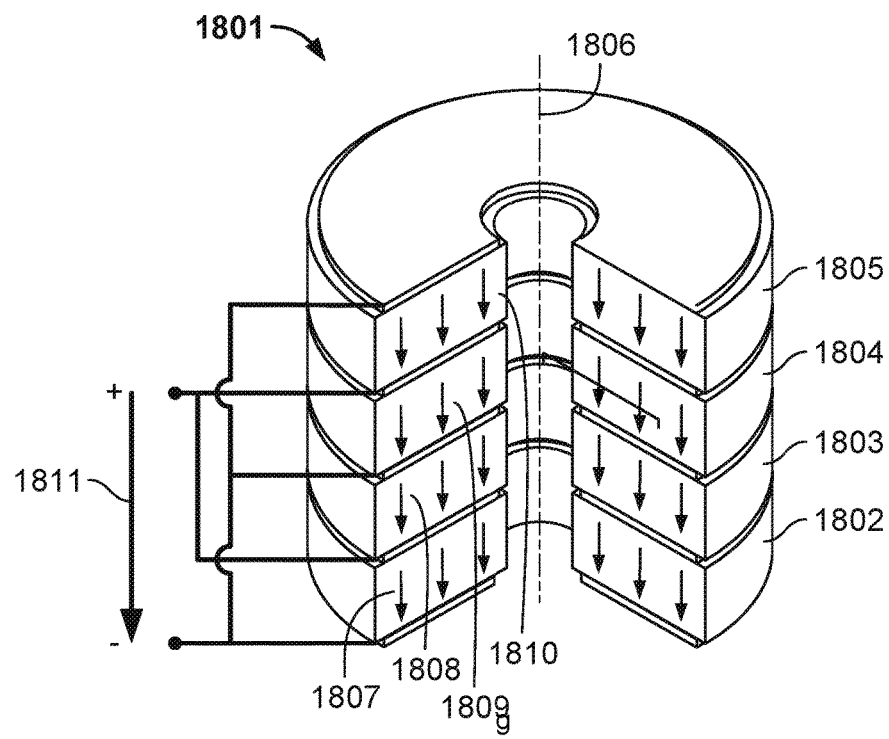
FIG. 18 is a diagram illustrating an embodiment of a cutaway view of a stacked piezoelectric transducer with four annular transducer layers configured for one-port operation having piezoelectric polling directions aligned between adjacent layers.

FIG. 18 is a diagram illustrating an embodiment of a cutaway view of a stacked piezoelectric transducer with four annular transducer layers configured for one-port operation having piezoelectric polling directions aligned between adjacent layers. In the example shown, first piezoelectric polling direction 1807 points in substantially the same direction as applied electric field 1811 within first piezoelectric layer 1802, second piezoelectric polling direction 1808 points in substantially the opposite direction as applied electric field 1811 within second piezoelectric layer 1803, third polling piezoelectric direction 1809 points in substantially the same direction as applied electric field 1811 within third piezoelectric layer 1804, and fourth piezoelectric polling direction 1810 points in substantially the opposite direction as applied electric field 1811 within fourth piezoelectric layer 1805. When the frequency of time-varying applied electric field 1811 corresponds to the frequency of an axial mode of vibration of stacked transducer 1801, stacked transducer 1801 operates preferentially in an even numbered axial extensional mode (e.g., a fourth axial extensional mode or an eighth axial extensional mode) about axis 1806.

In some embodiments, although not depicted explicitly in a figure, it is understood that more than four layers, each having a polling direction alternately pointing in the same and opposite direction as an applied electric field may be stacked, and that such a transducer stack may operate preferentially in a corresponding vibrational mode of the resulting overall stack. For example, a stacked transducer with six transducer layers preferentially operates in a sixth axial extensional mode of the overall stack. The number of layers in a transducer stack is chosen, for example, to scale the electrical impedance of the transducer stack, to scale one or more natural frequencies of the transducer stack, or to scale the available actuation effort.

Figure 19:
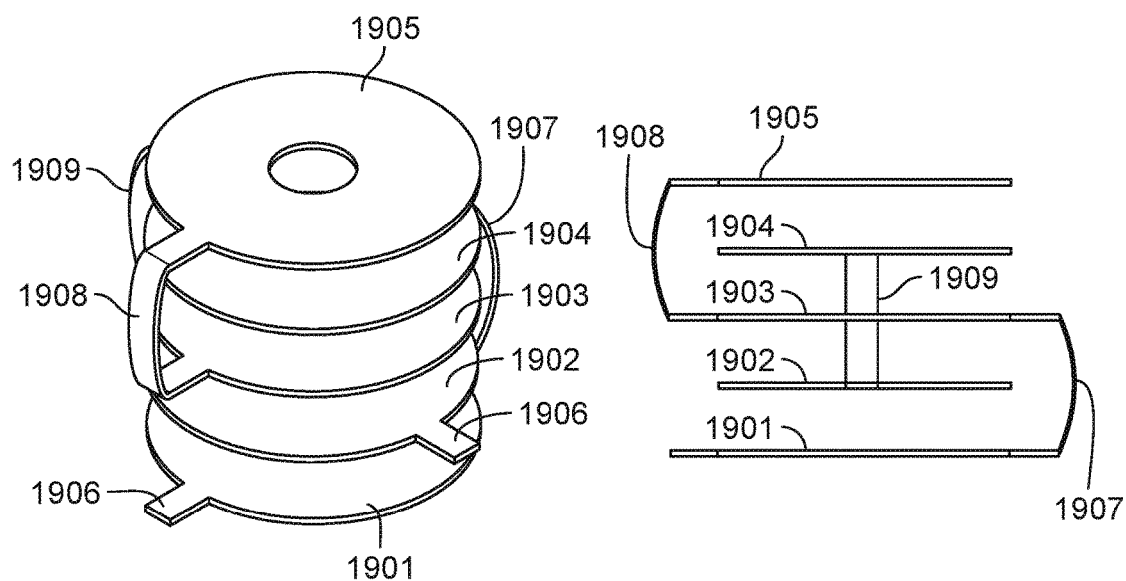
FIG. 19 are diagrams illustrating an embodiment of isometric and side views of an electrode scheme that is used to support one-port operation of a stacked transducer with four transducer layers.

FIG. 19 is a diagram illustrating an embodiment of isometric and side views of an electrode scheme that is used to support one-port operation of a stacked transducer with four transducer layers. In some embodiments, the electrodes are used with a stacked piezoelectric transducer with four annular transducer layers (e.g., stacked piezoelectric transducer 1701 of FIG. 17 or stacked piezoelectric transducer 1801 of FIG. 18). In the example shown, first electrode 1901 and second electrode 1902 include leads 1906 to facilitate forming electrical connections with various components. Third electrode 1903 is connected to first electrode 1901 by means of first connector 1907 and to fifth electrode 1905 by second connector 1908. Second electrode 1902 is connected to fourth electrode 1904 by means of third connector 1909. In various embodiments, a connector is formed using either the same material as an electrode or as a separate element (e.g., a length of conductive wire) and subsequently joined to one or more electrodes (e.g., using a solder, brazing, or conductive epoxy based process). In various embodiments, an electrode, a lead, or a connector is formed using an electrically conductive material using one or more of the following metals: beryllium copper, aluminum, copper, nickel, molybdenum, tungsten, ruthenium, or any other appropriate metal. Typical values for the thickness of an electrode or connector are 10 µm to 1 mm.

Figure 20:
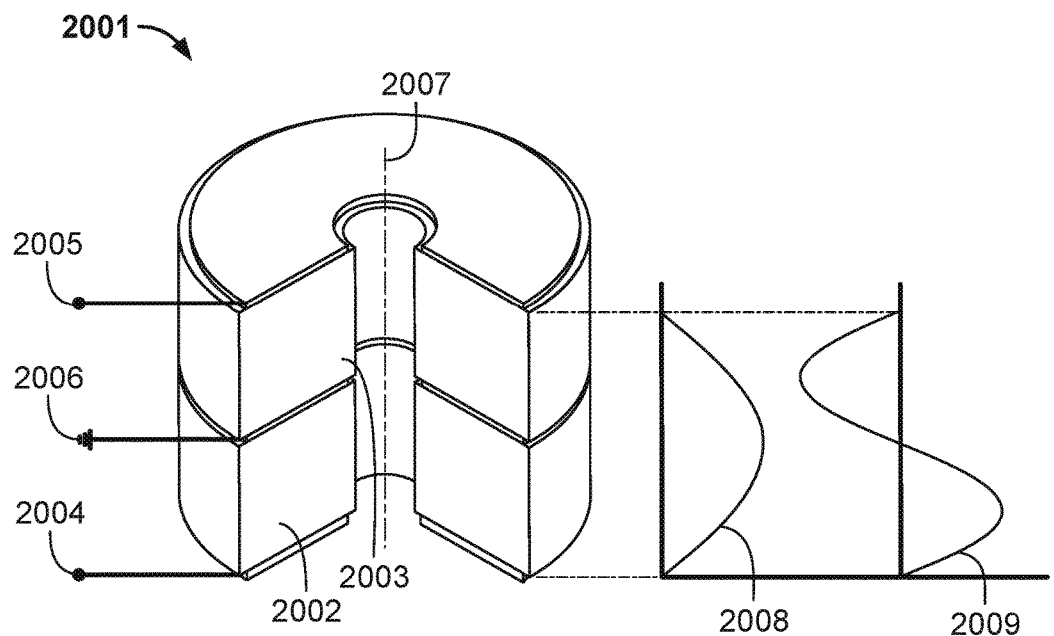
FIG. 20 is a diagram illustrating an embodiment of a cutaway view of a stacked piezoelectric transducer with two annular transducer layers configured for two-port operation.

FIG. 20 is a diagram illustrating an embodiment of a cutaway view of a stacked piezoelectric transducer with two annular transducer layers configured for two-port operation. In the example shown, first electrical port 2004 is proximate to a first surface of first piezoelectric layer 2002, connection to electrical ground 2006 is proximate to a second surface of first piezoelectric layer 2002 and to a first surface of second piezoelectric layer 2003. Second electrical port 2005 is proximate to a second surface of second piezoelectric layer 2003. In a two-port configuration, the input and output signals are mechanically coupled and substantially electrically isolated (parasitic capacitive coupling may exist). In various configurations, first piezoelectric layer 2002 has the same piezoelectric polarization direction as second piezoelectric layer 2003, or has the opposite piezoelectric polarization direction as second piezoelectric layer 2003. In various embodiments, an electrical drive signal is applied to first port 2004 and a resulting sense signal is measured at second port 2005, an electrical drive signal is applied to second port 2005 and a resulting sense signal is measured at first port 2004, or any other appropriate operation mode. When the frequency of a time-varying drive signal corresponds to the frequency of an axial mode of vibration of stacked transducer 2001, stacked transducer 2001 operates preferentially in an axial extensional mode of vibration (e.g., first axial extensional mode 2008 or second axial extensional mode 2009) about axis 2007.

Figure 21:
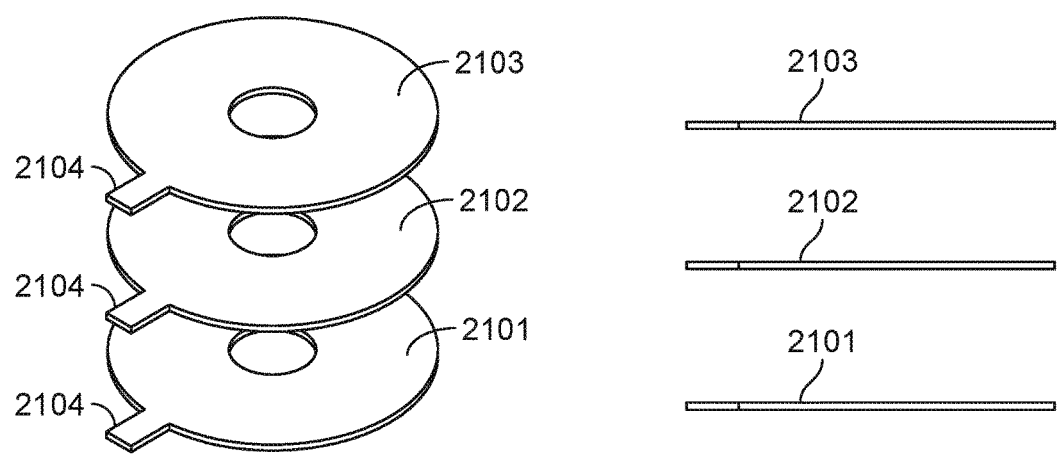
FIG. 21 are diagrams illustrating an embodiment of isometric and side views of an electrode scheme that is used to support two-port operation of a piezoelectric transducer having two piezoelectric layers.

FIG. 21 is a diagram illustrating an embodiment of isometric and side views of an electrode scheme that is used to support two-port operation of a piezoelectric transducer having two piezoelectric layers. In the example shown, first electrode 2101, second electrode 2102, and third electrode 2103 have leads 2104 that are used to support two-port operation of a piezoelectric transducer having two piezoelectric layers. In various embodiments, lead 2104 is formed either using the same material as an electrode or as a separate element (e.g., a length of conductive wire) and subsequently joined to one or more electrodes (e.g., using a solder, brazing, or conductive epoxy based process). In various embodiments, an electrode or a lead is formed using an electrically conductive material using one or more of the following metals: beryllium copper, aluminum, copper, nickel, molybdenum, tungsten, ruthenium, or any other appropriate metal. Typical values for the thickness of an electrode or lead are 10 µm to 1 mm.

Figure 22:
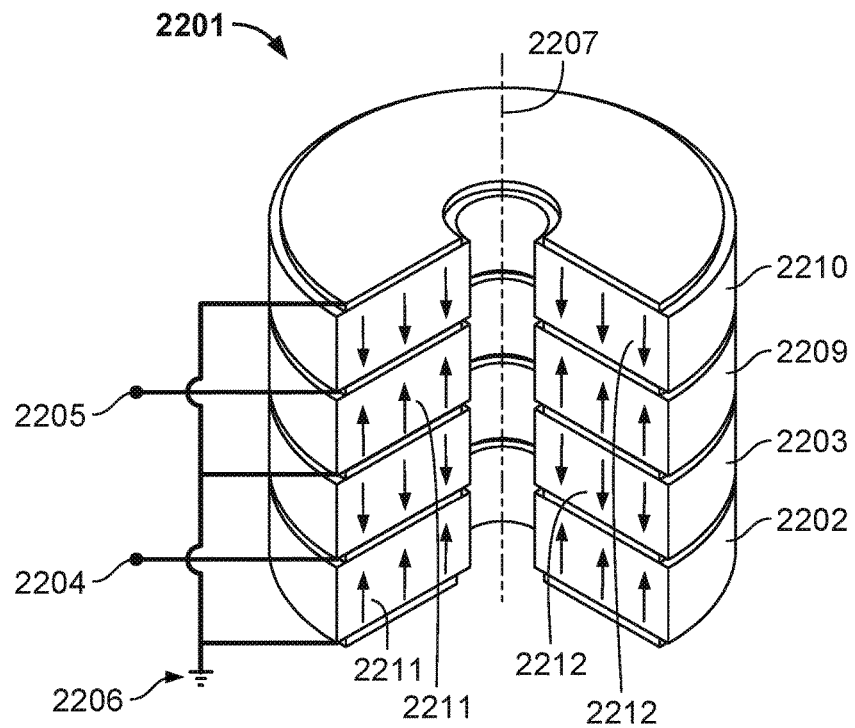
FIG. 22 is a diagram illustrating an embodiment of a cutaway view of a stacked piezoelectric transducer with four annular transducer layers configured for two-port operation.

FIG. 22 is a diagram illustrating an embodiment of a cutaway view of a stacked piezoelectric transducer with four annular transducer layers configured for two-port operation. In the example shown, connection to electrical ground 2206 is proximate to a first surface of first piezoelectric layer 2202. First electrical port 2204 is proximate to a second surface of first piezoelectric layer 2202 and a first surface of second piezoelectric layer 2203. Connection to electrical ground 2206 is proximate to a second surface of second piezoelectric layer 2203 and a first surface of third piezoelectric layer 2209. Second electrical port 2205 is proximate to a second surface of third piezoelectric layer 2209 and a first surface of fourth piezoelectric layer 2210. Connection to ground 2206 is proximate to a second surface of fourth piezoelectric layer 2210. In some embodiments, first piezoelectric layer 2202 and third piezoelectric layer 2209 have first piezoelectric polarization direction 2211, and second piezoelectric layer 2203 and fourth piezoelectric layer 2210 have second piezoelectric polarization direction 2212. In various embodiments, an electrical drive signal is applied to first port 2204 and a resulting sense signal is measured at second port 2205, an electrical drive signal is applied a second port 2205 and a resulting sense signal is measured at first port 2204, or any other appropriate operating mode. When the frequency of a time-varying drive signal corresponds to the frequency of an axial mode of vibration of stacked transducer 2201, stacked transducer 2201 operates preferentially in a corresponding axial extensional mode of vibration about axis 2207.

Figure 23:
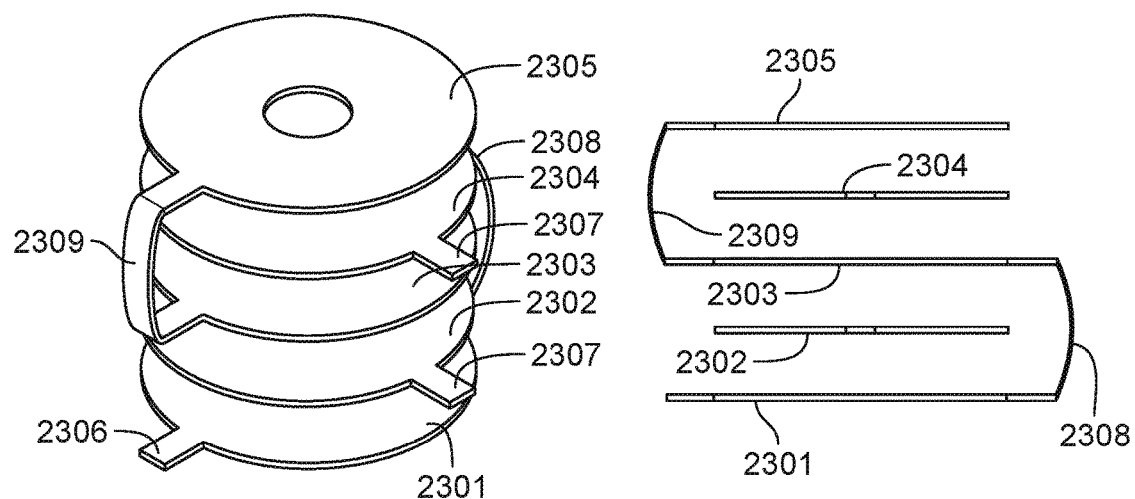
FIG. 23 are diagrams illustrating an embodiment of isometric and side views of an electrode scheme that is used to support two-port operation of a stacked transducer with four transducer layers.

FIG. 23 is a diagram illustrating an embodiment of isometric and side views of an electrode scheme that is used to support two-port operation of a stacked transducer with four transducer layers. In some embodiments, the electrodes are used with a stacked piezoelectric transducer with four annular transducer layers (e.g., stacked piezoelectric transducer 2201 of FIG. 22). In the example shown, first electrode 2301 includes lead 2306 to facilitate forming electrical connections to ground. Second electrode 2302 and fourth electrode 2304 include leads 2307 to facilitate forming electrical connections between a first and second electrical port and various components. Third electrode 2303 is connected to first electrode 2301 by means of first connector 2308 and to fifth electrode 2305 by second connector 2309. In various embodiments, a connector is formed using the same material as an electrode or as a separate element (e.g., a length of conductive wire) and subsequently joined to one or more electrodes (e.g., using a solder, brazing, or conductive epoxy based process). In various embodiments, an electrode, a lead, or a connector is formed using an electrically conductive material using one or more of the following metals: beryllium copper, aluminum, copper, nickel, molybdenum, tungsten, ruthenium, or any other appropriate metal. Typical values for the thickness of an electrode or connector are 10 µm to 1 mm.

The depicted embodiments are merely representative configurations of a stacked piezoelectric transducer and other combinations of the above described concepts are understood to fall within the scope of the present disclosure.

In various embodiments, piezoelectric transducer layers have the same thicknesses, electrodes have the same thicknesses, piezoelectric transducer layers have different thicknesses, electrodes have different thicknesses, or any other appropriate combination. Tailoring the thickness of each transducer layer may maximize the strength of the electromechanical coupling of a stacked piezoelectric transducer, particularly when a resonant strain profile within a stack is modified by the presence of additional elements, such as an acoustic termination, horn, flange, or sample. In some embodiments, a post is provided to constrain the individual layers of a stacked transducer along an axial axis.

Acoustic Termination

Figure 24:
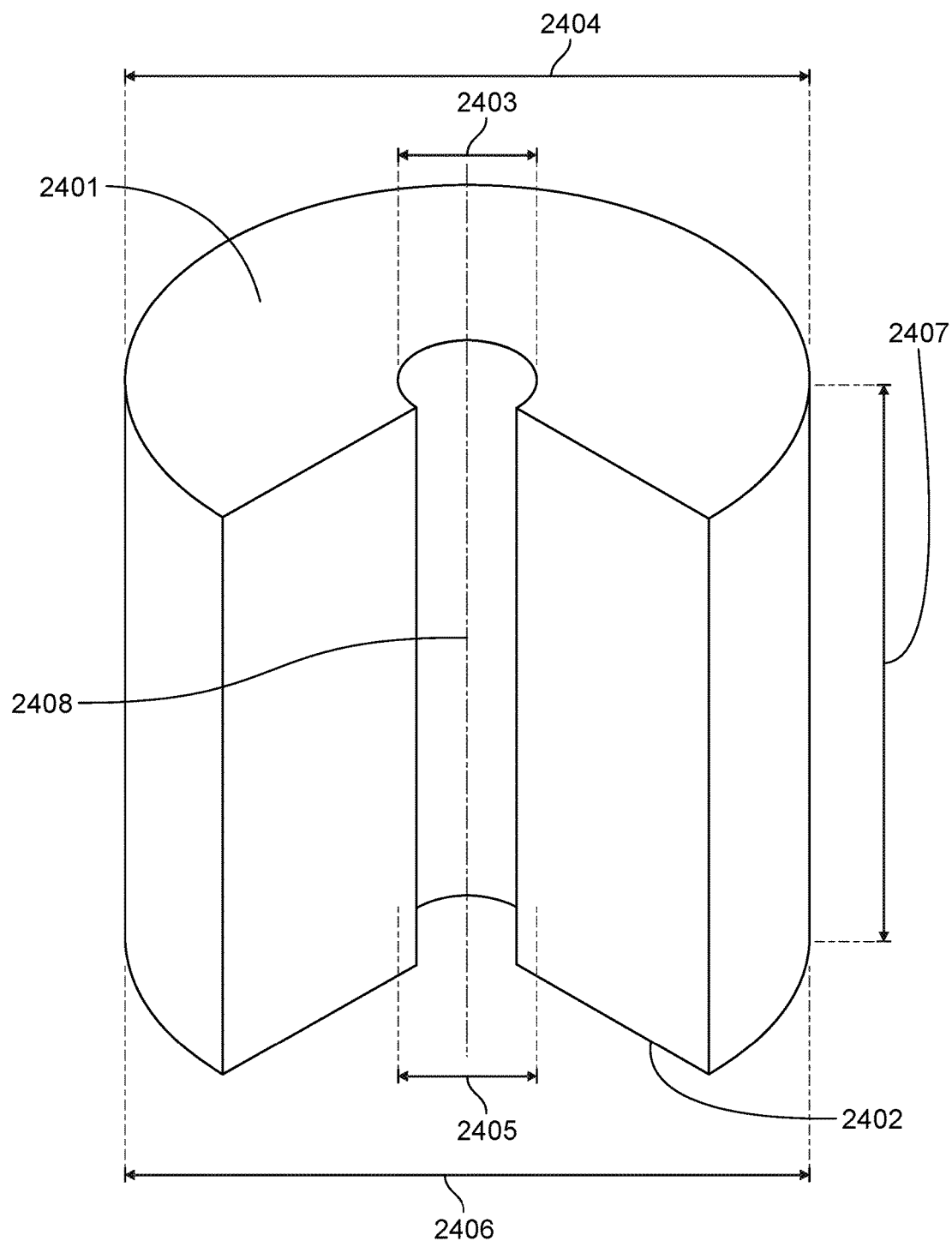
FIG. 24 is a diagram illustrating an embodiment of an acoustic termination layer or cap.

FIG. 24 is a diagram illustrating an embodiment of an acoustic termination layer or cap. In the example shown, an acoustic termination is provided to tailor a standing wave pattern associated with a resonance of an overall system comprising a yield strength measurement instrument and a sample. An acoustic termination has first end 2401 with first inner diameter 2403 and first outer diameter 2404, and second end 2402 with second inner diameter 2405 and second outer diameter 2406. In some embodiments, second end 2402 is proximate to a transducer. First end 2401 and second end 2402 of an acoustic termination are substantially parallel and separated by length 2407. In various embodiments, first inner diameter 2403 and second inner diameter 2405 are zero (corresponding to a disk acoustic termination), first inner diameter 2403 and second inner diameter 2405 are substantially non-zero (corresponding to an annular acoustic termination). In various embodiments, first outer diameter 2404 and second outer diameter 2406 are substantially equal (corresponding to a cylindrical acoustic termination layer), first outer diameter 2404 and second outer diameter 2406 are not equal (corresponding to a tapered acoustic termination). In some embodiments, an acoustic termination comprises one or more layers arranged along axis 2408. In various embodiments, the one or more layers are formed using the same or different materials. For example, the acoustic termination comprises alternating layers of a material with a relatively lower acoustic impedance and a material with a relatively higher acoustic impedance. In some embodiments, the thickness of each of the one or more layers of an ultrasonic termination is approximately equal to an integer number of quarter wavelengths of a resonant mode of the overall instrument-sample system. For example, the number, material, and thickness of the one or more layers in an acoustic termination are chosen to increase the efficiency of a transducer or to reduce a maximum or average elastic stress magnitude within a transducer. In various embodiments, an acoustic termination is formed using one or more of the following materials: beryllium copper, an aluminum, a titanium, a steel alloy, or any other appropriate material.

Figure 25:
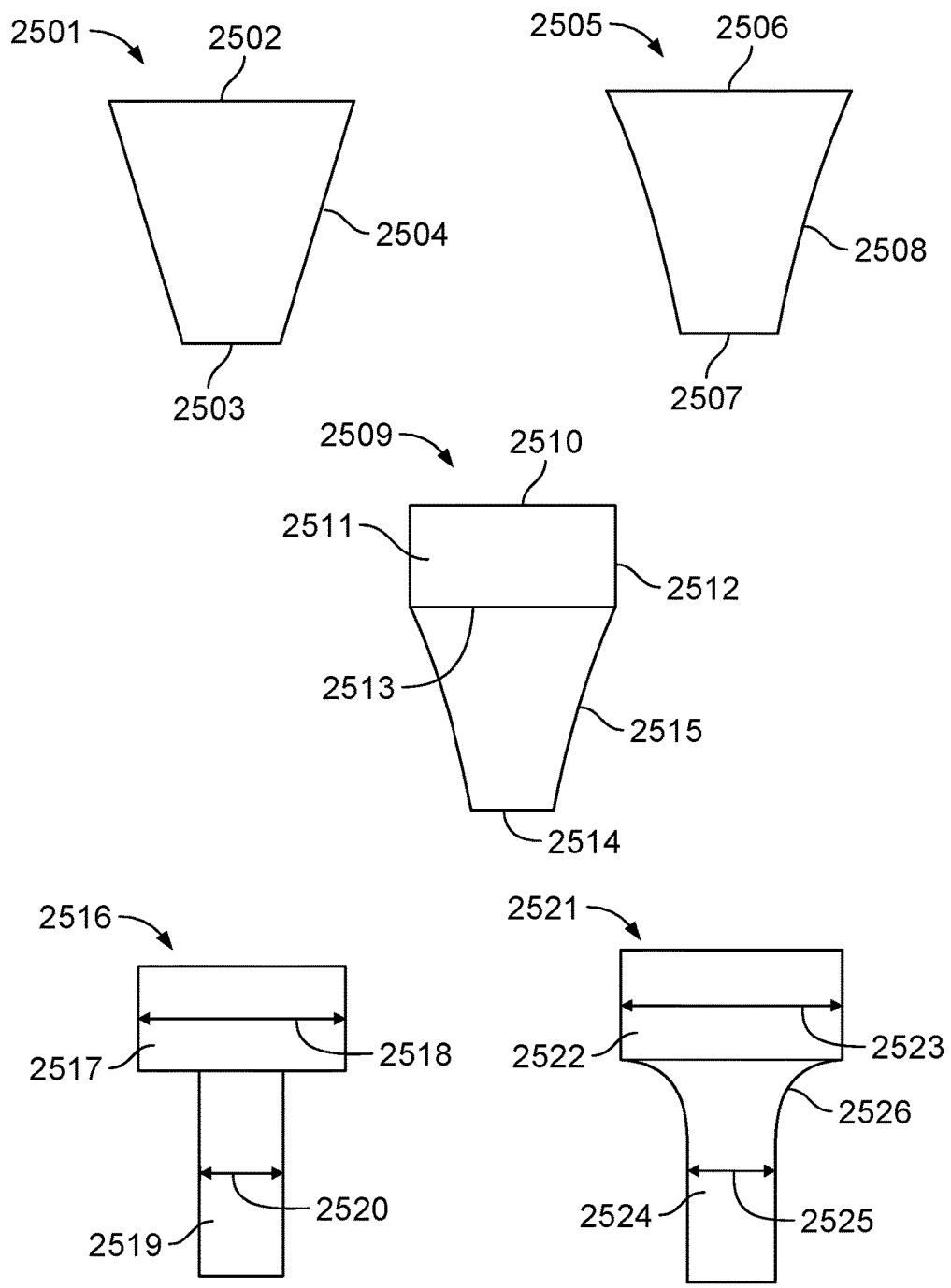
FIG. 25 are diagrams illustrating embodiments of cross sectional views of acoustic waveguides having different profiles.

FIG. 25 is a diagram illustrating an embodiment of cross sectional views of acoustic waveguides having different profiles. In the examples shown, linear taper 2501 has first end 2502 and second end 2503, parallel to the first end, that are separated by constant taper 2504. Exponential taper 2505 has first end 2506 and second end 2507, parallel to the first end, that are separated by exponential taper 2508. Composite cylindrical-exponential taper 2509 has a first section having first end 2510 and second end 2511, parallel to the first end, that are separated by perpendicular length 2512, and a second section having first end 2513 and second end 2514, parallel to the first end, that are separated by exponential taper 2515. Stepped cylindrical acoustic waveguide 2516 has first section 2517 with first diameter 2518 and second section 2519 with second diameter 2520. Another stepped cylindrical acoustic waveguide 2521 has first section 2522 with first diameter 2523 and second section 2524, connected to the first section by fillet 2526, with second diameter 2525. In various embodiments, profiles for an acoustic waveguide include catenoidal, arbitrary polynomial, logarithmic, Bessel function, and any other appropriate profile or combination of profiles. In some embodiments, a composite acoustic waveguide has more than two sections. In some embodiments, an acoustic waveguide exhibit substantial axis symmetry about an axis perpendicular to a first end and a second end.

In various embodiments, an acoustic termination layer includes an acoustic waveguide that has a one or more of the following profiles: a cylinder, a linear taper, an exponential taper, a composite cylindrical-exponential taper, a stepped profile, or any other appropriate profile.

In some embodiments, a yield strength measurement instrument maintains a stack comprising at least one each of an acoustic termination, a transducer, and an acoustic horn in a state of compressive preload. In some embodiments, threaded fasteners are used to impart a desired preload. For example, a screw with external threads is mated with a nut or a tapped hole with corresponding internal threads to impart a compressive stress in proportion to an applied torque. In various embodiments, a preload is imparted by an external force such as a vise or a press, and the resulting state of compressive stress is maintained by a press fit, by a soldered, brazed or welded joint, or by an adhesive bond between mating elements (e.g., a pin or a rod and a hole or a slot. In some embodiments, a compressive preload of 10 to 50 MPa is preferred.

Figure 26:
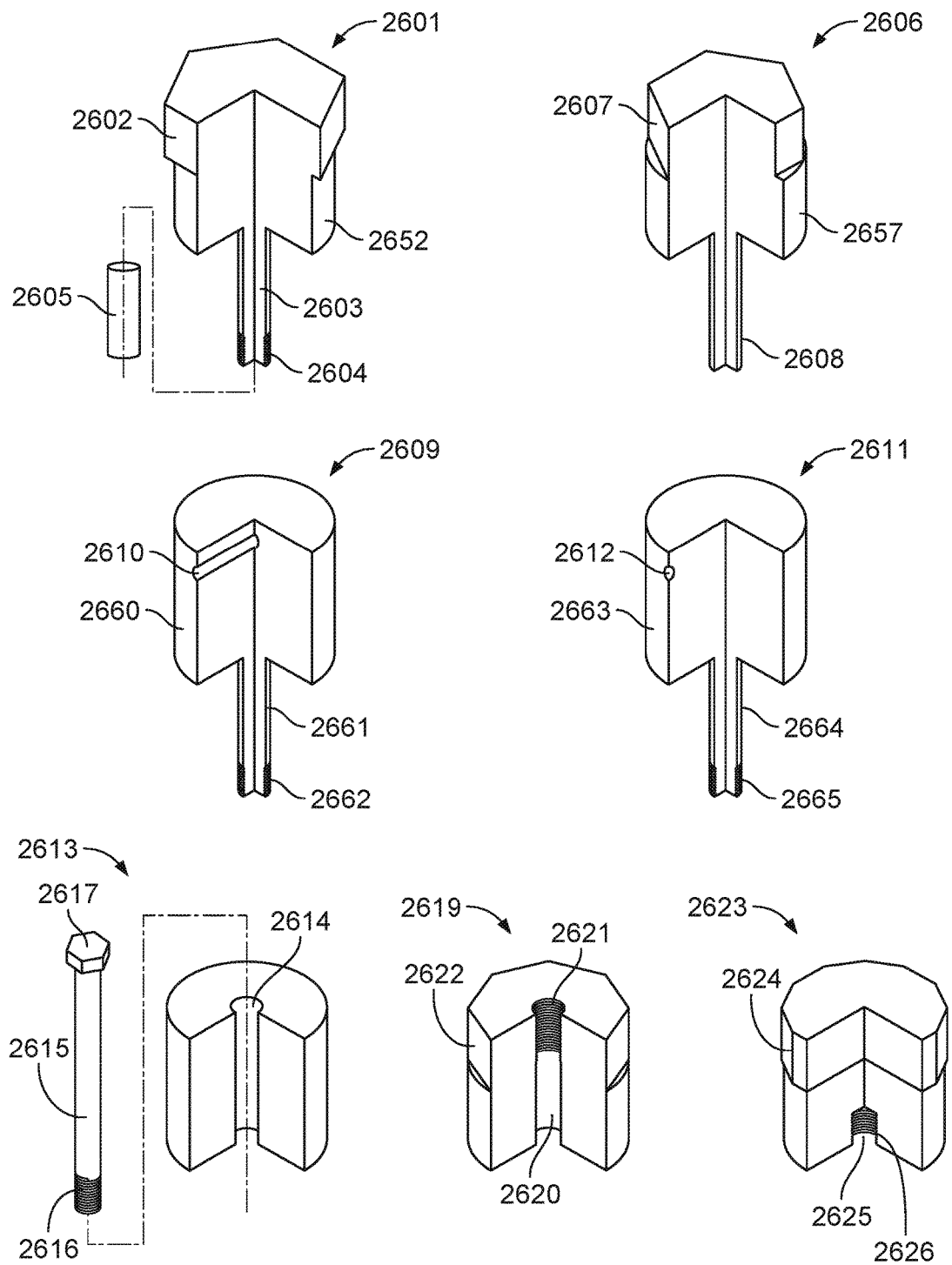
FIG. 26 are diagrams illustrating embodiments of a cutaway view of an acoustic termination layer or cap.

FIG. 26 are diagrams illustrating embodiments of a cutaway view of an acoustic termination layer or cap. In some of the examples shown, an acoustic termination layer includes one or more flat surfaces to facilitate applying an external torque to impart a compressive preload using a tool (e.g., a crescent wrench). Acoustic termination layer 2601 includes hexagonal head 2602 circumscribed around a cylindrical waveguide portion 2652 that couples to cylinder 2603 which terminates with threads 2604. Cylinder 2603 and threads 2604 are able to fit within insulating sleeve 2605 that fits within an inner diameter of a transducer to preload a transducer. Acoustic termination layer 2606 includes hexagonal head 2607 inscribed within a cylindrical waveguide portion 2657 that couples to cylinder 2608. Cylinder 2608 is able to fit within an inner diameter of a transducer to preload a transducer. Acoustic termination layer 2609 includes cylindrical head 2660 with transverse hole 2610 (for tightening/loosening acoustic termination layer 2609) that couples to cylinder 2661 which terminates with threads 2662. Cylinder 2661 and threads 2662 are able to fit within an inner diameter of a transducer to preload a transducer. Acoustic termination layer 2611 includes cylindrical head 2663 with dimple or recess 2612 (for tightening/loosening acoustic termination layer 2611) that couples to cylinder 2664 which terminates with threads 2665. Cylinder 2664 and threads 2665 are able to fit within an inner diameter of a transducer to preload a transducer.

In various embodiments, an acoustic termination layer does not include threads to support fastening the acoustic termination layer to the rest of a yield strength measurement instrument, but instead uses one or more of the following for fastening: a solder process, a brazing process, a welding process, an adhesive-based process, a press fit, or any other appropriate fastening method. In some embodiments, acoustic termination layer 2619 includes through-hole 2620 with internal threads 2621 to support fastening acoustic termination layer 2619 to the rest of a yield strength measurement instrument. In some embodiments, acoustic termination layer 2623 includes dodecahedral head 2624 and blind hole 2625 with internal threads 2626 to support fastening acoustic termination layer 2623 to the rest of a yield strength measurement instrument. In some embodiments, acoustic termination layer 2613 includes through-hole 2614 that accommodates screw 2615 with head 2617 for applying an external torque and external threads 2616 to support fastening acoustic termination layer 2613 to the rest of a yield strength measurement instrument. In some embodiments, an insulating sleeve (e.g., insulating sleeve 2605) surrounds a cylinder of an acoustic termination layer to insulate the cylinder from an electrode of a transducer.

Acoustic Horn Waveguide

In some embodiments, a suitably designed three-dimensional (3D) tapered elastic horn waveguide (or simply "horn") is used to focus vibrational energy from one or more ultrasonic transducers down to a reduced area on a surface of the test sample. In some embodiments, a horn is used to increase the overall system resonant quality factor (Q). In some embodiments, the horn mitigates the effects of intrinsic nonlinearities within the ultrasonic transducer, and thus facilitates the use of low-cost, commercially available components.

Figure 27:
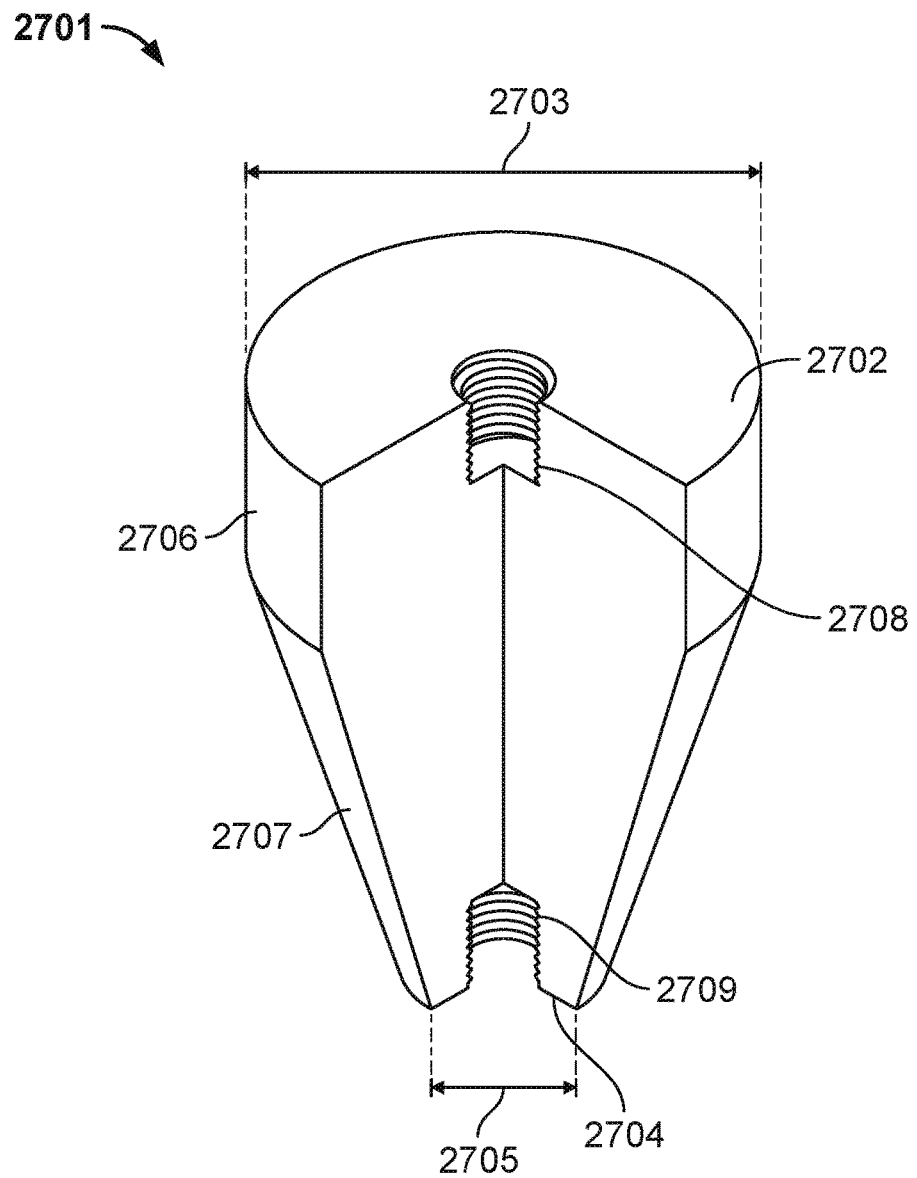
FIG. 27 is a diagram illustrating an embodiment of a cutaway view of a tapered horn waveguide.

FIG. 27 is a diagram illustrating an embodiment of a cutaway view of a tapered horn waveguide. In the example shown, horn 2701 has first end 2702 with first diameter 2703 and second end 2704, parallel to the first end, with second diameter 2705. In some embodiments, first end 2702 is proximate to a transducer and second end 2704 is proximate to a flange or a sample. In various embodiments, horn 2701 has one or more taper sections between first end 2702 and second end 2704 (e.g., a section with a smooth curve taper—for example, a linear, an exponential, a catenoidal, or a polynomial taper, sections that have discrete steps in the diameters, or any combination of the two). Horn 2701 has first taper section 2706 with a cylindrical taper and second taper section 2707 with a linear taper. Horn 2701 includes a feature on first end 2702 to facilitate forming a connection between horn 2701 and a transducer or acoustic termination (e.g., threaded blind hole 2708). Horn 2701 includes a feature on second end 2704 to facilitate forming a connection between horn 2701 and a flange or a sample (e.g., threaded blind hole 2709).

Figure 28:
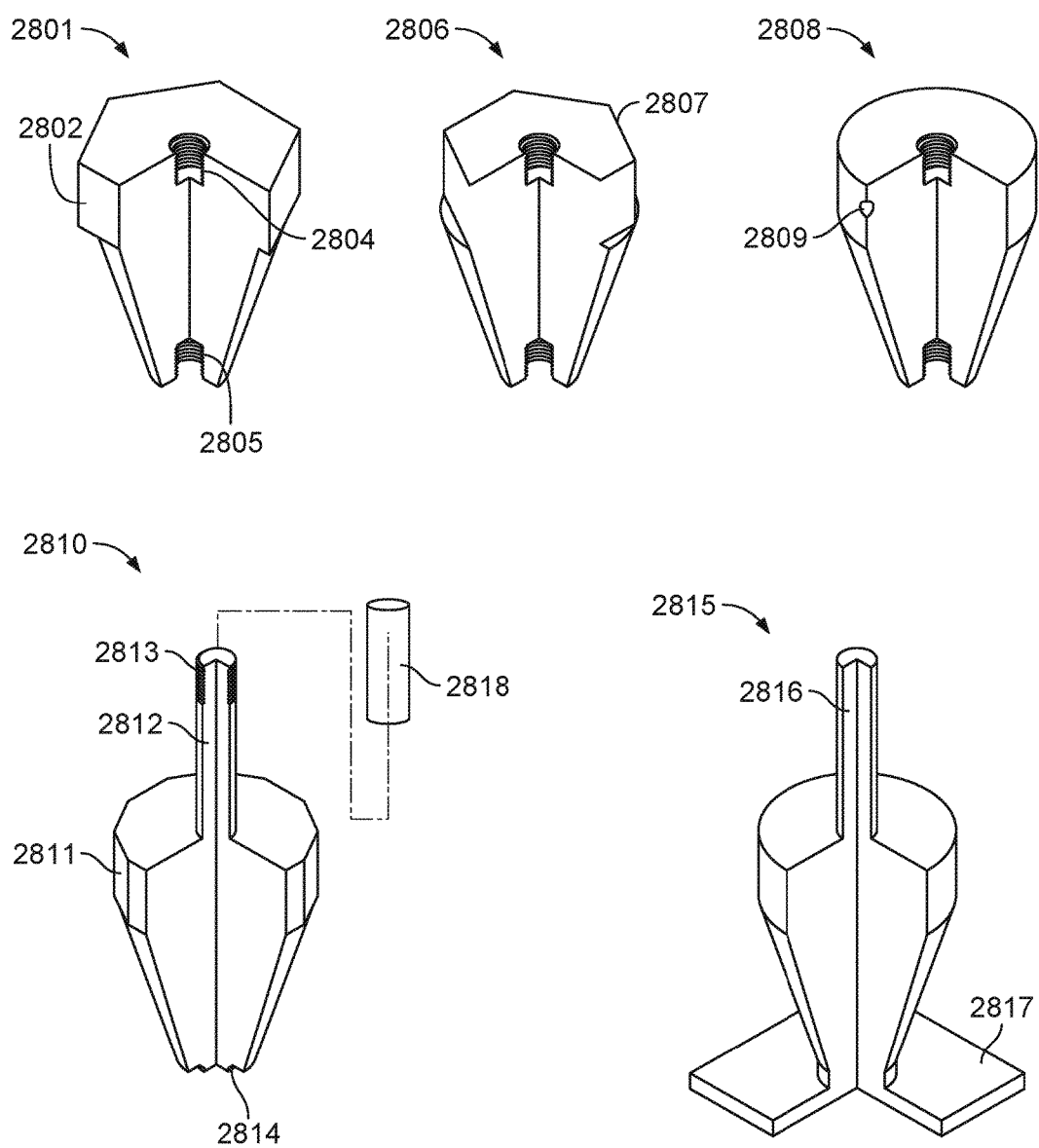
FIG. 28 are diagrams illustrating embodiments of a cutaway view of an acoustic horn waveguide.

FIG. 28 are diagrams illustrating embodiments of a cutaway view of an acoustic horn waveguide. In some of the examples shown, an acoustic horn includes one or more flat surfaces to facilitate applying an external torque to impart a compressive preload using a tool (e.g., a crescent wrench). Acoustic horn 2801 includes hexagonal head 2802 circumscribed around a cylindrical waveguide portion. Acoustic horn 2801 includes blind hole with internal threads 2804 to support fastening an acoustic horn to a transducer or acoustic termination and blind hole with internal threads 2805 to support fastening an acoustic horn to a flange or a sample. Acoustic horn 2806 includes hexagonal head 2807 inscribed within a cylindrical waveguide portion. Acoustic horn 2808 includes dimple or recess 2809 to facilitate applying an external torque to impart a compressive preload using a tool (e.g., a spanner wrench). Acoustic horn 2810 includes dodecagonal head 2811 circumscribed around a cylindrical waveguide portion. Acoustic horn 2810 includes monolithic screw 2812 with external threads 2813 to support fastening an acoustic horn to a transducer or acoustic termination. Acoustic horn 2810 includes monolithic screw with external threads 2814 to support fastening an acoustic horn to a flange or a sample. Acoustic horn 2815 includes monolithic post 2816 to support fastening an acoustic horn to a transducer or acoustic termination by means of a process (e.g., a solder process, a brazing process, a welding process, an adhesive-based process, etc.). Acoustic horn 2815 includes monolithic flange 2817. In various embodiments, screw 2812 or post 2816 includes insulating sleeve 2818 that is able to slip around screw 2812 or post 2816 in order to isolate acoustic horn from transducer electrodes.

In some embodiments, a length of a horn is tuned between a first end and second end to yield optimal measurement performance for a sample of a given thickness, elastic stiffness and mass density. For example, a length of a horn is specified to substantially correspond to an integer multiple of one quarter wavelength of a relevant mode of vibration or such that the overall acoustic path comprising two or more of a sample, a flange, a horn, a transducer and a termination substantially corresponds to an integer number of half wavelengths of a relevant wave mode. In various embodiments, a horn is substantially axisymmetric, or a horn is not substantially axisymmetric. In various embodiments, an acoustic horn is formed using one or more of the following:

beryllium copper, a titanium alloy (e.g., Ti-6Al-4V), a steel alloy, an amorphous zirconium based alloy, or any other metal or combination thereof.

Accommodating Planar, Cylindrical, and Spherical Samples

Figure 29:
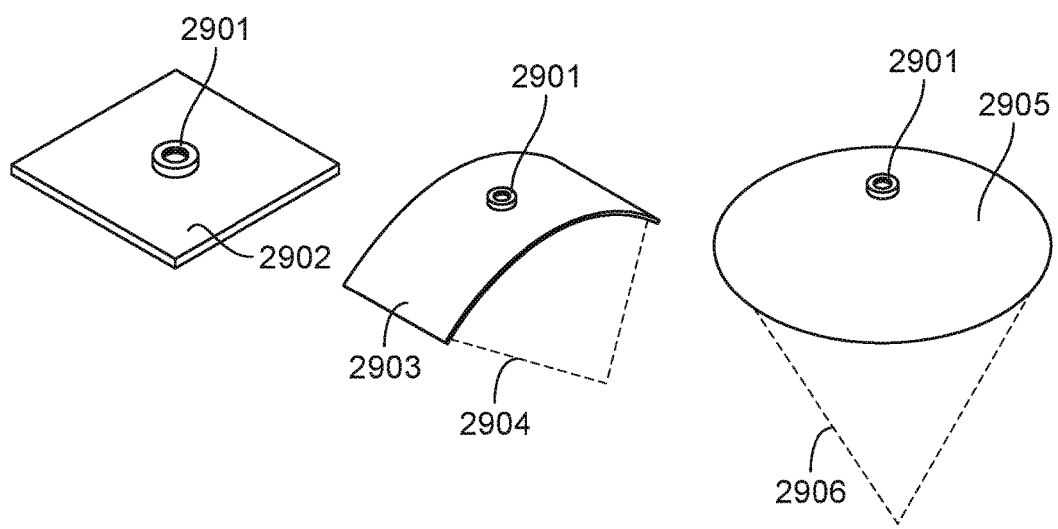
FIG. 29 is a diagram illustrating an embodiment of an example of a flange.

FIG. 29 is a diagram illustrating an embodiment of a flange. In some embodiments, a flange is located between an ultrasonic horn waveguide or transducer and a sample (e.g., an outer wall of a steel pipeline). In the example shown, the flange has fitting 2901 on a first end to support forming a connection between the flange and a transducer or ultrasonic horn. In various embodiments, fitting 2901 is a screw with external threads, is a bushing with internal threads, or any other appropriate fitting. In some embodiments, a flange is a monolithic extension of an acoustic horn waveguide or a transducer (e.g., monolithic flange 2817 of FIG. 28). In various embodiments, a flange is joined with an acoustic horn waveguide or a transducer using one of the following joining processes: a solder, a brazing, a welding, an adhesive-based process, or any other appropriate joining process. The second end of a flange is configured to at least partially match the profile of an intended target sample. For example, to test a planar sample (e.g., a plate), a second end of flange 2902 is itself planar. As another example, to test a cylindrical sample (e.g., a pipeline wall) of a certain outer radius, a second end of flange 2903 is itself a section of a cylinder of substantially the same radius (e.g., radius 2904). As still another example, to test a spherical sample (e.g., a pressure vessel) of a certain outer radius, a second end of flange 2905 is itself a section of a sphere of substantially the same radius (e.g., radius 2906). In various embodiments, a second end of a flange includes one or more through-holes to facilitate screwing, bolting, riveting the flange securely to a sample, or any other appropriate manner of attaching the flange to the sample. In various embodiments, a flange is formed using, one or more of the following metals: beryllium copper, an aluminum alloy, a titanium alloy, a steel alloy, or any other appropriate metal.

Approaches to Mitigate Losses Associated with Laterally Propagating Waves

In various embodiments, an ultrasonic yield strength measurement instrument employs a measurement approach based on making observations of waveforms in the vicinity of frequencies corresponding to standing wave patterns (or resonances) induced across the thickness of a sample by a transducer system. Laterally propagating waves that "bleed" energy away to the surrounding regions of the sample (e.g., outside of the intended effective test control volume) may be detrimental to the overall sensor performance. The following are one or more approaches to mitigate losses associated with laterally propagating waves escaping the intended test control volume.

Reflector Flange

Figure 30:
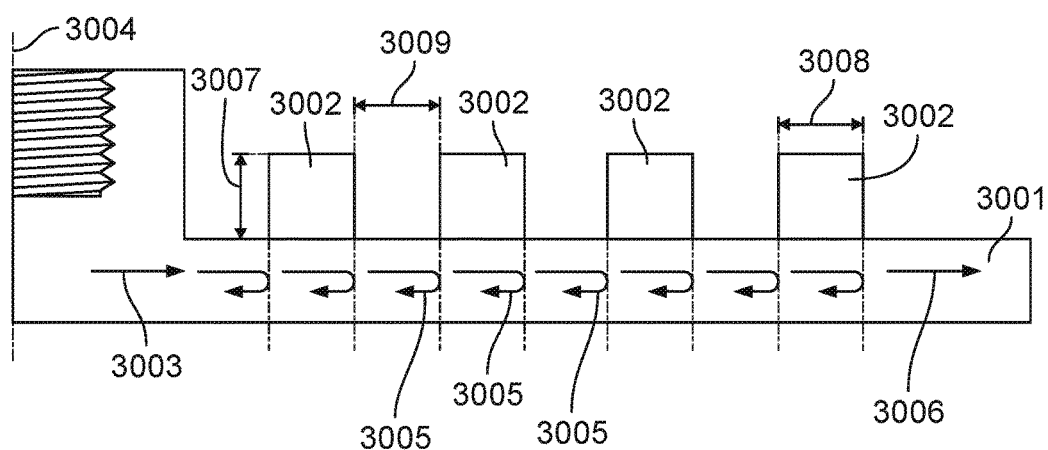
FIG. 30 is a diagram illustrating an embodiment of a cross-sectional view of a flange having one or more reflectors to mitigate an undesired loss of vibrational energy associated with laterally propagating waves.

FIG. 30 is a diagram illustrating an embodiment of a cross-sectional view of a flange having one or more reflectors to mitigate an undesired loss of vibrational energy associated with laterally propagating waves. In the example shown, a portion of incident vibrational energy 3003 is propagating radially away from an axial axis 3004 that is proximate to a horn or transducer. The presence and absence of reflectors 3002 presents a region of relatively higher and lower acoustic impedance, respectively. Thus, the portion of the vibrational energy 3005 incident at each transition between a region with and without reflectors 3002 is reflected in proportion to the magnitude of the impedance change, and the magnitude of a transmitted wave 3006 is reduced accordingly. Each of reflectors 3002 has height 3007 extending out of the plane of flange 3001, width 3008 in the plane of flange 3001, and space 3009 separating it from an adjacent reflector. It is advantageous to tune width 3008 and space 3009 of a reflector to optimize its ability to mitigate losses associated with laterally propagating waves. For example, width 3008 and space 2009 of a reflector are each specified to substantially correspond to an integer multiple of one quarter wavelength of a relevant mode of vibration. In some embodiments, the number of reflectors 3002 on flange 3001 is between 2 and 10. In some embodiments, a reflector is formed using a material having a relatively high acoustic impedance (e.g., tungsten, silicon carbide, molybdenum, etc.).

Figure 31:
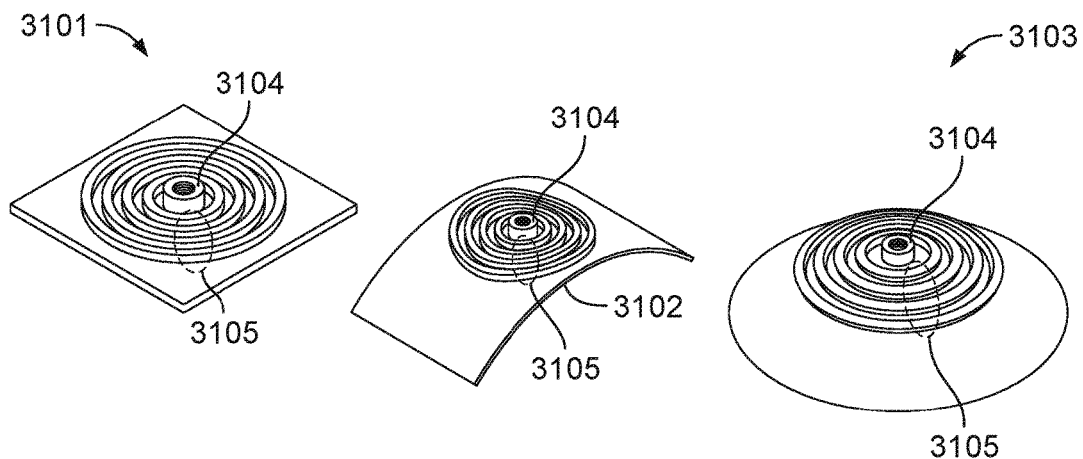
FIG. 31 are diagrams illustrating embodiments of a flange configured to accommodate planar, cylindrical, and spherical samples.

FIG. 31 are diagrams illustrating embodiments of a flange configured to accommodate planar, cylindrical, and spherical samples. In the example shown, flange 3101 is configured to accommodate a planar sample. Flange 3102 is configured to accommodate a cylindrical sample. Flange 3103 is configured to accommodate a spherical sample. Flange 3101, flange 3102, and flange 3103 each include one or more concentric acoustic reflectors 3105 substantially sharing an axial axis with bushing 3104.

Energy Trapping Flange

In some embodiments, an ultrasonic yield strength measurement system utilizes standing "S1" Rayleigh-Lamb wave patterns to infer the elastic properties of the test sample. These wave modes are said to be "dispersive," meaning their propagation velocity can depend on their cyclic frequency. The dispersive behavior of these modes is tailored through the design of a flange such that the resulting wave number (or propagation constant) is real (corresponding to a propagating wave) within the test volume proximate to a flange, and imaginary (corresponding to a reflected wave) outside of it. In this manner, the vibrational energy imparted by the ultrasonic transducer is substantially confined to the virtual cylinder (with exponentially decaying tails) of the pipeline wall that defines the effective sample volume. In some embodiments, the desired energy trapping is realized by contouring a flange such that it is thicker within a region proximate to the active test volume, and thinner within a region beyond the active test region. In some other embodiments, the desired energy trapping is realized by contouring a flange such that it is thinner within a region proximate to the active test volume, and thicker within a region beyond the active test region. In some embodiments, the present yield strength measurement device utilizes other dispersive resonant wave modes (e.g., horizontally-polarized shear ("SH") waves, surface waves, interface waves, etc.) that are also be substantially confined to a region proximate to a flange by contouring a flange as described above. In general, multiple wave modes are transduced within a given ultrasonic yield strength measurement device and the mode of operation is understood to refer to a particular mode of interest.

Overall Measurement System

Figure 32A:
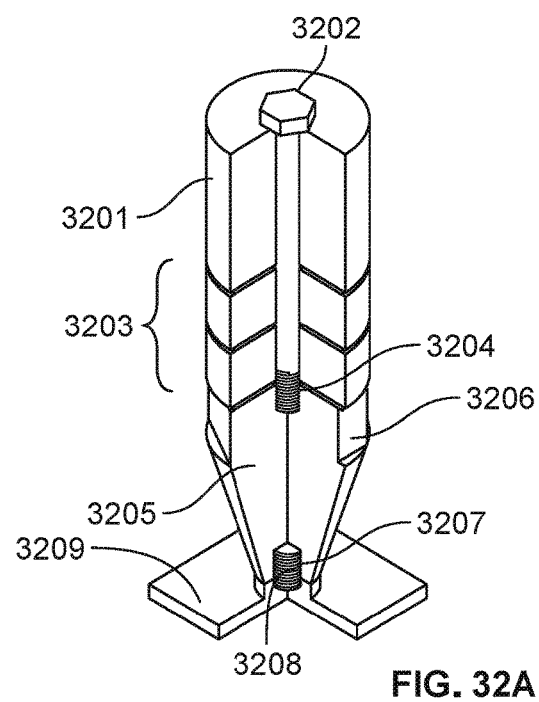
FIG. 32A is a diagram illustrating an embodiment of cutaway views of an ultrasonic yield strength measurement system configured to measure the elastic properties of a planar sample.

FIG. 32A is a diagram illustrating an embodiment of a cutaway view of an ultrasonic yield strength measurement system configured to measure the elastic properties of a planar sample. In the example shown, an ultrasonic yield strength measurement system includes acoustic termination layer 3201 connected to blind hole with internal threads 3204 on acoustic horn 3205 using screw 3202. Screw 3202 passes through a coaxial through-hole of transducer 3203. Transducer 3203 comprises two annular piezoelectric layers disposed between three electrodes. Acoustic horn 3205 includes blind hole with internal threads 3207 that is used to connect acoustic horn 3205 to a bushing on flange 3209 using a stud with external threads 3208. Acoustic horn 3205 includes hexagonal flats 3206 to facilitate applying an external torque to impart a corresponding compressive preload across a stack comprising acoustic termination 3201, transducer 3203 and acoustic horn 3205.

Figures 32B, 32C:
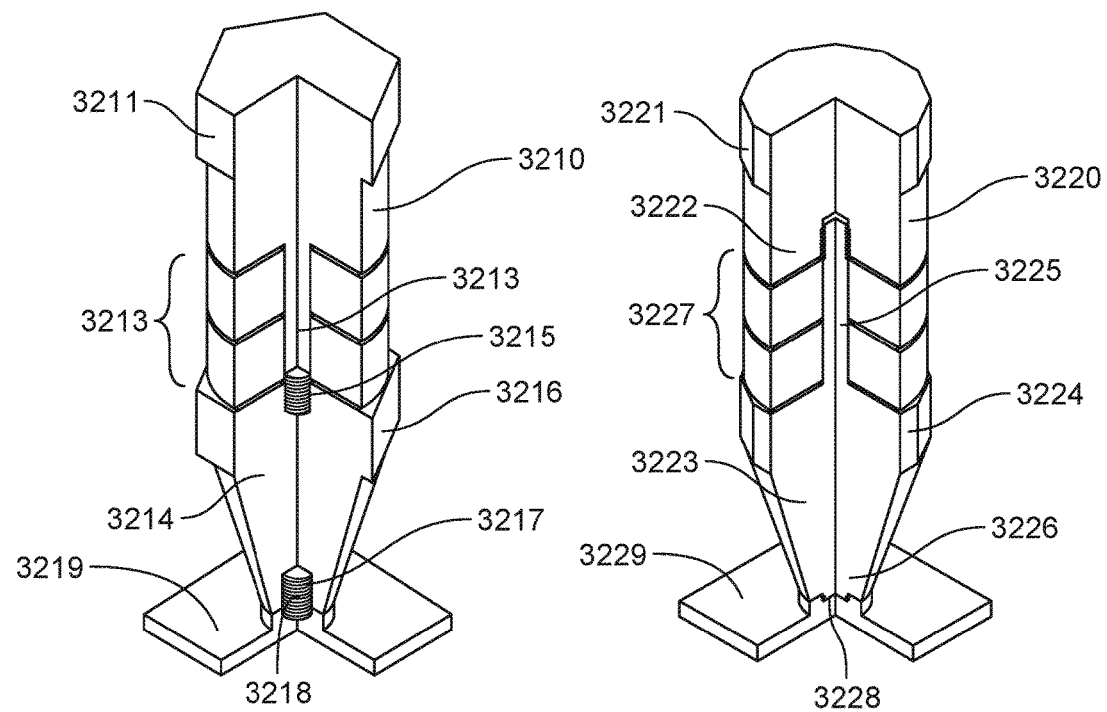
FIG. 32B is a diagram illustrating an embodiment of cutaway views of a second ultrasonic yield strength measurement system configured to measure the elastic properties of a planar sample.
FIG. 32C is a diagram illustrating an embodiment of cutaway views of a third ultrasonic yield strength measurement system configured to measure the elastic properties of a planar sample.

FIG. 32B is a diagram illustrating an embodiment of a cutaway view of an ultrasonic yield strength measurement system configured to measure the elastic properties of a planar sample. In the example shown, an ultrasonic yield strength measurement system includes acoustic termination layer 3210 connected to blind hole with internal threads 3215 on acoustic horn 3214 using monolithic screw 3213. Monolithic screw 3213 passes through a coaxial throughhole of transducer 3213. Transducer 3213 comprises two annular piezoelectric layers disposed between three electrodes. Acoustic horn 3214 includes blind hole with internal threads 3217 that is used to connect acoustic horn 3214 to a bushing on flange 3219 using stud with external threads 3218. Acoustic termination layer 3210 and acoustic horn 3214 include hexagonal flats 3211 and hexagonal flats 3216, respectively, to facilitate applying an external torque to impart a corresponding compressive preload across a stack comprising acoustic termination 3210, transducer 3213 and acoustic horn 3214.

FIG. 32C is a diagram illustrating an embodiment of a cutaway view of an ultrasonic yield strength measurement system configured to measure the elastic properties of a planar sample. In the example shown, an ultrasonic yield strength measurement system includes acoustic termination layer 3220 with blind hole with internal threads 3222 connected to monolithic screw 3225 on acoustic horn 3223. Monolithic screw 3225 passes through a coaxial throughhole of transducer 3227. Transducer 3227 comprises two annular piezoelectric layers disposed between three electrodes. Acoustic horn 3223 includes screw with internal threads 3226 that is used to connect acoustic horn 3223 to bushing with internal threads 3228 on flange 3229. Acoustic termination layer 3220 and acoustic horn 3223 include dodecagonal flats 3221 and dodecagonal flats 3224, respectively, to facilitate applying an external torque to impart a corresponding compressive preload across a stack comprising acoustic termination 3220, transducer 3227 and acoustic horn 3223.

Figure 33A:
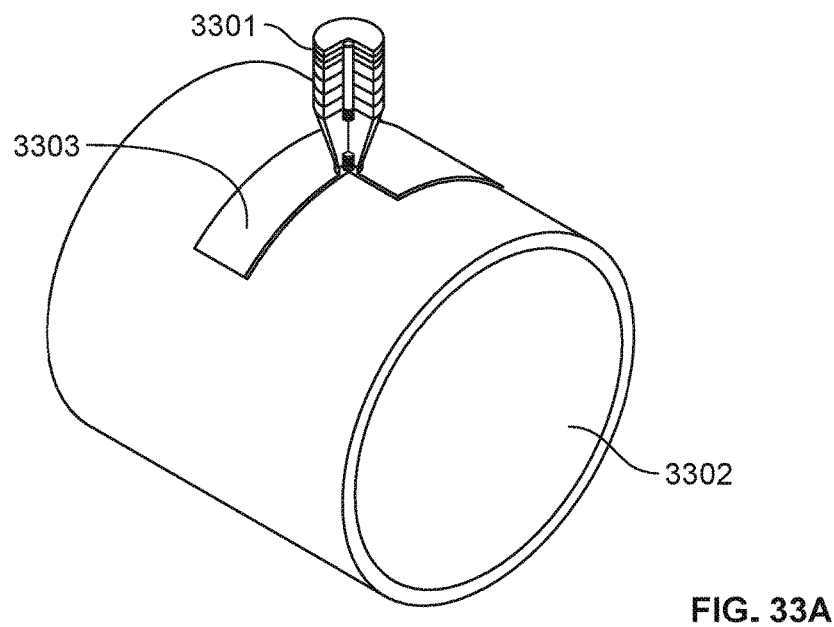
FIG. 33A is a diagram illustrating an embodiment of a cutaway view of an ultrasonic yield strength measurement instrument configured to measure a cylindrical sample positioned on cylindrical pipeline segment.

FIG. 33A is a diagram illustrating an embodiment of a cutaway view of an ultrasonic yield strength measurement instrument configured to measure a cylindrical sample positioned on cylindrical pipeline segment. Flange 3303 is positioned on cylindrical pipeline segment 3302 in order that ultrasonic yield strength measurement instrument 3301 is able to measure yield strength of cylindrical pipeline segment 3302.

Figure 33B:
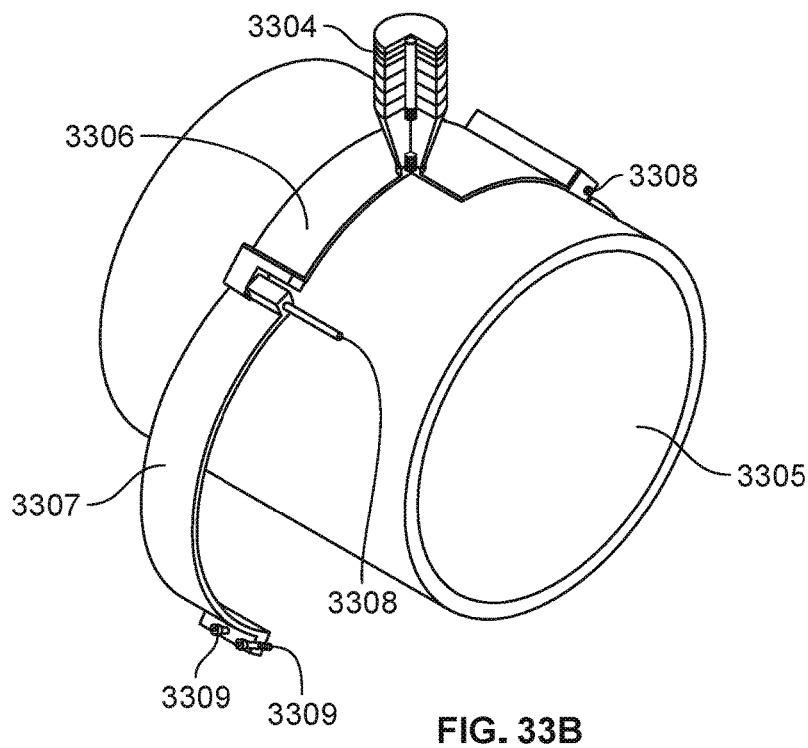
FIG. 33B is a diagram illustrating an embodiment of a cutaway view of an ultrasonic yield strength measurement instrument configured to measure a cylindrical sample secured to a cylindrical pipeline segment using a collar.

FIG. 33B is a diagram illustrating an embodiment of a cutaway view of an ultrasonic yield strength measurement instrument configured to measure a cylindrical sample secured to a cylindrical pipeline segment using a collar. In the example shown, ultrasonic yield strength measurement instrument 3304 is configured with flange 3306 that is positioned on cylindrical pipeline segment 3305. Collar 3307 is provided to secure the acoustically active portion of a yield strength measurement instrument to a sample during a measurement procedure. Collar 3307 is in a two piece "gullwing" configuration wherein each piece connects to edge 3308 of flange 3306, circumscribes an angular sector of cylindrical sample 3305, and is secured to the other using a fastener (e.g., using screws 3309). In some embodiments, a collar is in a one piece configuration wherein a first end of the collar connects to a first edge of a flange, circumscribes an angular sector of a cylindrical sample, and is secured at second end to a second edge of the flange using one or more fasteners (e.g., using screws and/or bolts).

In various configurations, a flange, an acoustic horn, or a transducer is secured directly to a sample using, one or more of the following: a threaded fastener, a solder process, a brazing process, a welding process, an adhesive-based process, or any other appropriate securing manner.

Sample

In various embodiments, a sample has a first surface proximate to a flange, a horn, or a transducer and a second end proximate to a gas or vacuum ambient environment. For example, a sample comprises a region flat plate, a cylindrical pipe, or a spherical pressure vessel. In addition to steel alloys, examples of other possible sample materials include metals such aluminum, titanium, copper, and their alloys. In some embodiments, an ultrasonic yield strength measurement tool is configured to measure samples of a range of thicknesses (e.g., from 2 to 30 mm). In some embodiments, a couplant is used between a flange and a sample to enhance the transmission of ultrasonic waves across the flange-sample interface. In various embodiments, a couplant comprises one or more of the following liquids and gels: water, silicone oil, propylene glycol, glycerin, or any other appropriate couplant.

Signal Generation, Processing and Computation

In some embodiments, a yield strength measurement device includes elements for signal generation (e.g., a signal generator, a power amplifier, a power booster, etc.). In some embodiments, a yield strength measurement tool includes elements for signal processing and computation (e.g., a transimpedance amplifier, an attenuator, a digital signal processor (DSP), an analog-to-digital converter (ADC), a digital-to-analog converter (DAC), a memory, a microprocessor, a micro-controller, etc.). In some embodiments, a yield strength measurement tool includes a user interface, a battery and a power transformer. In some embodiments, the components for signal processing, computation, user interface and power supply are housed in a remote enclosure separate from the acoustically-active measurement hardware. In some embodiments, a DSP provides an ability to compensate for environmental factors such as ambient temperature and vibration.

Figure 34:
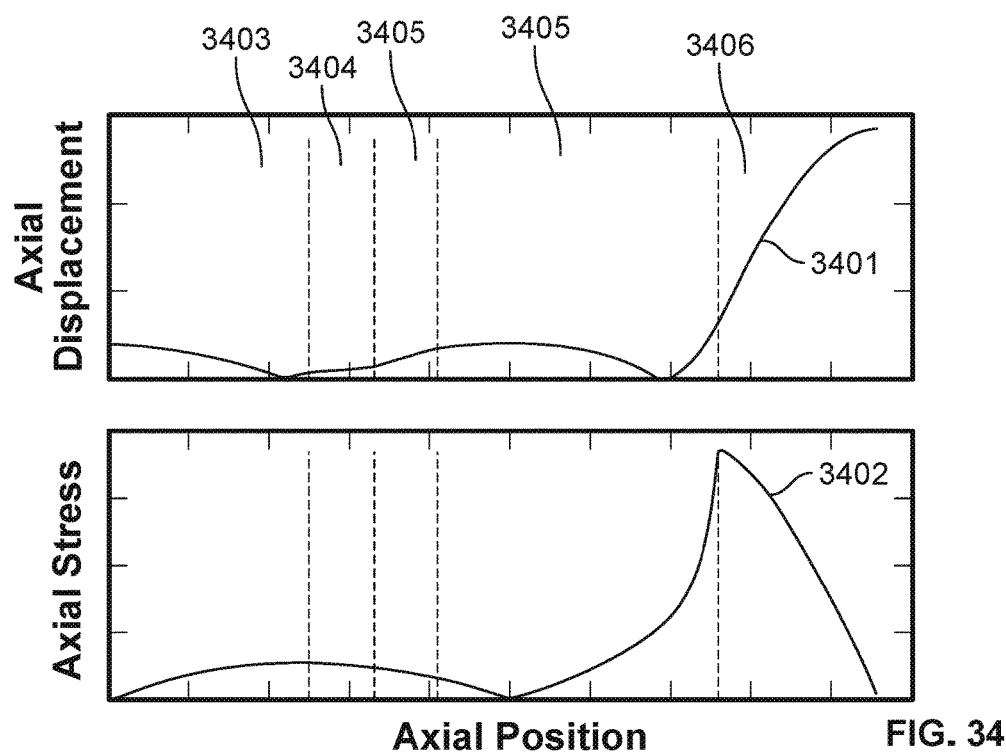
FIG. 34 is a graph illustrating an embodiment of an axial displacement and stress within an ultrasonic yield strength measurement instrument plotted against axial position along a horizontal axis.

FIG. 34 is a graph illustrating an embodiment of an axial displacement and stress within an ultrasonic yield strength measurement instrument plotted against axial position along a horizontal axis. In the example shown, axial displacement 3401 and stress 3402 within an ultrasonic yield strength measurement instrument are plotted against axial position along a horizontal axis. Demarcations between acoustic termination layer 3403, transducer layer 3404, composite horn waveguide 3405 and sample 3406 are shown as dashed vertical lines. In order to provide accurate measurements of the yield strength of a sample, the nonlinear response induced by ultrasonic vibrations within the sample must be much greater than the nonlinear response induced within the measurement instrument itself. Thus, the acoustic horn is designed to amplify the stress within transducer 3404 to a substantially higher (e.g., 5 to 20 times) value within sample 3406. In the example shown, the peak axial stress within sample 3406 is approximately seven times greater than the peak axial stress within ultrasonic transducer 3404.

Figure 35A:
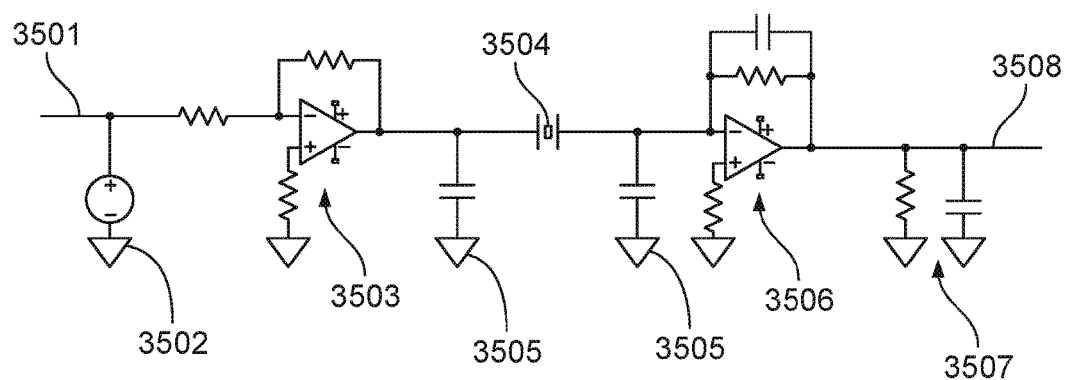
FIG. 35A is a schematic illustrating an embodiment of a circuit configured for interfacing with a yield strength measurement instrument employing a one-port transducer.

FIG. 35A is a schematic illustrating an embodiment of a circuit configured for interfacing with a yield strength measurement instrument employing a one-port transducer. In the example shown, signal generator 3502 generates input signal 3501 that is amplified by power amplifier 3503. An input signal comprises a substantially periodic time varying potential with a frequency between 10 kHz and 100 kHz and with an amplitude between 1 Volt and 10 Volts. Cables (e.g., coaxial cables) characterized by capacitance 3505 connect one-port transducer 3504 to the output of power amplifier 3503 and to an input of transimpedance amplifier 3506. Power amplifier 3503 amplifies the magnitude of an input signal by a factor of 5 to 50 (e.g., to between 50 Volts and 500 Volts) and transimpedance amplifier 3506 has an output signal between 1 Volt and 20 Volts. Output signal 3508 is measured using an instrument (e.g., a voltmeter or an oscilloscope) that is characterized by impedance 3507.

Figure 35B:
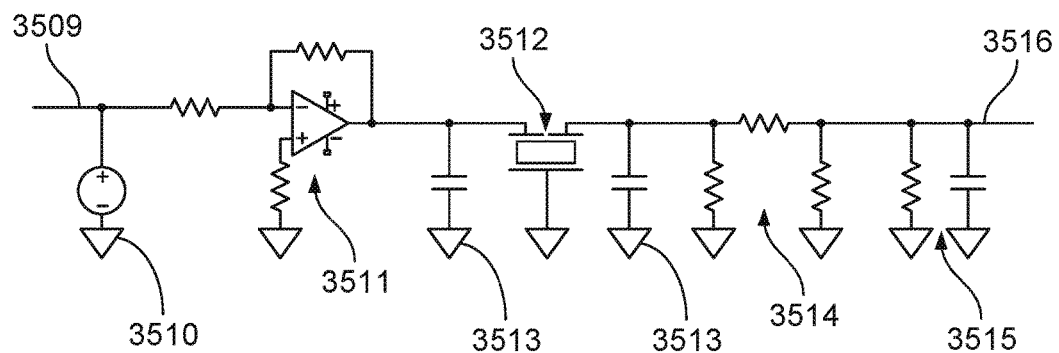
FIG. 35B is a schematic illustrating an embodiment of a circuit configured for interfacing with a yield strength measurement instrument employing a two-port transducer.

FIG. 35B is a schematic illustrating an embodiment of a circuit configured for interfacing with a yield strength measurement instrument employing a two-port transducer. In the example shown, signal generator 3510 generates input signal 3509 that is amplified by power amplifier 3511. Input signal is a substantially periodic time varying potential with a frequency between 10 kHz and 100 kHz and with an amplitude between 1 Volt and 10 Volts. Cables (e.g., coaxial cables) characterized by capacitance 3513 connect two-port transducer 3512 to the output of power amplifier 3511 and to voltage attenuator circuit 3514. Power amplifier 3511 amplifies the magnitude of an input signal by a factor of 5 to 50 (e.g., to between 50 Volts and 500 Volts) and voltage attenuator circuit 3514 has an output signal between 1 Volt and 20 Volts. Output signal 3516 is measured using an instrument (e.g., a voltmeter or an oscilloscope) that is characterized by impedance 3515.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for determining a material property, comprising
    an actuator, wherein the actuator is capable of generating a continuous wave ultrasonic excitation;
    a sensor configured to:
    measure a set of material responses corresponding to a set of ultrasonic excitations, wherein the set of material responses includes measurements to enable determination of a peak response for each of the set of ultrasonic excitations to create a set of peak responses, wherein the set of ultrasonic excitations includes ultrasonic excitations at a plurality of amplitudes and at a plurality of frequencies, wherein each of the set of ultrasonic excitations is of a continuous wave type and is applied using the actuator; and
    a processor configured to:
    determine the set of peak response for each of the set of ultrasonic excitations; and
    determine the material property of a material using the set of peak responses.

2. A system as in 1, wherein a first peak response associated with a first amplitude of the plurality of amplitudes is determined by providing an ultrasonic excitation of the first amplitude at the plurality of frequencies and measuring for each frequency of the plurality of frequencies a material response and determining the first peak response associated with a first amplitude of the plurality of amplitudes using the material response for each frequency of the plurality of frequencies and an associated first peak response frequency for the first amplitude.

3. A system as in 2, wherein the set of peak responses includes a corresponding peak response for each of the plurality of amplitudes and a corresponding peak response frequency for each of the plurality of amplitudes.

4. A system as in 3, wherein the material property comprises yield strength.

5. A system as in 4, wherein the yield strength is determined by relating the corresponding peak response frequency for each of the plurality of amplitudes to a nonlinear stiffness coefficient of the material.

6. A system as in 3, wherein the material property comprises Young's Modulus.

7. A system as in 6, wherein the Young's Modulus is determined by relating a linear response level peak response frequency corresponding to a linear response level peak response at a linear response level excitation with a linear response level amplitude to a wave propagation velocity of the material.

8. A system as in 1, further comprising a transducer for providing an ultrasonic excitation of the set of ultrasonic excitations.

9. A system as in 8, wherein the transducer comprises a piezoelectric transducer.

10. A system as in 9, wherein the piezoelectric transducer comprises a stacked piezoelectric transducer.

11. A system as in 10, wherein a polling direction of each layer of the stacked piezoelectric transducer is one of the following: the same direction or alternating directions.

12. A system as in 8, wherein the transducer comprises an ultrasonic transducer, wherein the ultrasonic transducer converts a time varying electric signal into a time varying mechanical strain and converts a time varying mechanical strain into a time varying electric signal.

13. A system as in 1, wherein the peak responses correspond to resonant ultrasonic wave modes in the material.

14. A system as in 1, wherein an acoustic termination is provided to tailor a resonant strain profile of a mode of vibration.

15. A system as in 1, wherein an ultrasonic horn is provided to guide vibrational energy from a relatively larger area of an ultrasonic transducer as compared to a relatively smaller area of a flange coupled to the material or a sample of the material.

16. A system as in 1, wherein a flange is provided to enable transfer an ultrasonic excitation of the set of ultrasonic excitations originating from a transducer to a sample of the material.

17. A system as in 16, wherein a collar is provided to securely attach the flange to the sample of the material.

18. A system as in 15, wherein the flange includes at least a first region contoured to provide an energy trapping effect on laterally propagating waves.

19. A system as in 15, wherein the flange includes at least a first acoustic reflector to mitigate losses associated with laterally propagating waves.

20. A method for determining a material property, comprising
    receiving a set of material responses corresponding to a set of ultrasonic excitations, wherein the set of material responses includes measurements to enable determination of a peak response for each of the set of ultrasonic excitations to create a set of peak responses, wherein the set of ultrasonic excitations includes ultrasonic excitations at a plurality of amplitudes and at a plurality of frequencies, wherein each of the set of ultrasonic excitations is of a continuous wave type and is applied using an actuator, wherein the actuator is capable of generating a continuous wave ultrasonic excitation;

determining, using a processor, the set of peak response for each of the set of ultrasonic excitations; and determining the material property of a material using the set of peak response for each of the set of ultrasonic excitations.

21. A computer program product for determining a material property, the computer program product being embodied in a non-transitory computer readable storage medium and comprising computer instructions for:

receiving a set of material responses corresponding to a set of ultrasonic excitations, wherein the set of material responses includes measurements to enable determination of a peak response for each of the set of ultrasonic excitations to create a set of peak responses, wherein the set of ultrasonic excitations includes ultrasonic excitations at a plurality of amplitudes and at a plurality of frequencies, wherein each of the set of ultrasonic excitations is of a continuous wave type and is applied using an actuator, wherein the actuator is capable of generating a continuous wave ultrasonic excitation;

determining, using a processor, the set of peak response for each of the set of ultrasonic excitations; and determining the material property of a material using the set of peak response for each of the set of ultrasonic excitations.

\* \* \* \* \*